United States Patent
Sharkey et al.

(10) Patent No.: US 9,717,544 B2
(45) Date of Patent: Aug. 1, 2017

(54) SUBCHONDRAL TREATMENT OF JOINT PAIN

(71) Applicant: ZIMMER KNEE CREATIONS, INC., Exton, PA (US)

(72) Inventors: Peter F. Sharkey, Villanova, PA (US); Charles F. Leinberry, Chester Springs, PA (US); Steven B. Cohen, Media, PA (US); Charanpreet S. Bagga, Basking Ridge, NJ (US); Erik M. Erbe, Rancho Santa Fe, CA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 36 days.

(21) Appl. No.: 14/617,058

(22) Filed: Feb. 9, 2015

(65) Prior Publication Data
US 2015/0150616 A1 Jun. 4, 2015

Related U.S. Application Data

(63) Continuation of application No. 12/950,355, filed on Nov. 19, 2010, now Pat. No. 8,951,261.
(Continued)

(51) Int. Cl.
*A61B 17/88* (2006.01)
*A61B 17/16* (2006.01)
(Continued)

(52) U.S. Cl.
CPC ...... *A61B 17/8805* (2013.01); *A61B 17/1637* (2013.01); *A61B 17/1697* (2013.01);
(Continued)

(58) Field of Classification Search
CPC ............ A61B 17/8805; A61B 17/1697; A61B 17/8894
See application file for complete search history.

(56) References Cited

U.S. PATENT DOCUMENTS 2,697,433 A 12/1954 Zehnder, Max A
3,913,187 A 10/1975 Okuda
(Continued)

FOREIGN PATENT DOCUMENTS

CN 101048111 A 10/2007
CN 101102724 A 1/2008
(Continued)

OTHER PUBLICATIONS

U.S. Appl. No. 12/950,230, Notice of Allowance mailed Oct. 7, 2015, 5 pgs.
(Continued)

*Primary Examiner* — Christian Sevilla
(74) *Attorney, Agent, or Firm* — Schwegman Lundberg & Woessner, P.A.

(57) ABSTRACT

The embodiments provide devices and methods that both strengthen the bone and stimulate the bone. Bone fractures or non-unions are stabilized, integrated or healed, which results in reduction of a bone defect, such as a bone marrow lesion or edema. In addition, the distribution of forces in a joint are restored or altered to relieve pain. In general, a joint is evaluated by taking an image of the joint and one or more subchondral defects are detected. At least one of the subchondral defects may be diagnosed as the source of pain and an extent of treatment for the subchondral defect is determined. The disclosed devices and techniques are particularly suited for treating chronic defects or injuries, where the patient's natural healing response has not resolved the defect. The present disclosure also provides several exemplary treatment modalities for the different extents of treatment needed.

20 Claims, 22 Drawing Sheets

Related U.S. Application Data

(60) Provisional application No. 61/263,170, filed on Nov. 20, 2009, provisional application No. 61/292,979, filed on Jan. 7, 2010, provisional application No. 61/300,337, filed on Feb. 1, 2010, provisional application No. 61/310,897, filed on Mar. 5, 2010, provisional application No. 61/311,152, filed on Mar. 5, 2010, provisional application No. 61/311,632, filed on Mar. 8, 2010, provisional application No. 61/324,931, filed on Apr. 16, 2010, provisional application No. 61/354,100, filed on Jun. 11, 2010, provisional application No. 61/377,313, filed on Aug. 26, 2010.

(51) Int. Cl.
*A61B 90/00* (2016.01)
*A61B 17/17* (2006.01)
*A61B 17/68* (2006.01)
*A61B 17/90* (2006.01)

(52) U.S. Cl.
CPC ...... *A61B 17/1764* (2013.01); *A61B 17/8897* (2013.01); *A61B 90/39* (2016.02); *A61B 17/17* (2013.01); *A61B 17/1742* (2013.01); *A61B 17/1775* (2016.11); *A61B 17/1778* (2016.11); *A61B 17/68* (2013.01); *A61B 17/8802* (2013.01); *A61B 17/8872* (2013.01); *A61B 2017/90* (2013.01)

(56) References Cited

U.S. PATENT DOCUMENTS

| | | | |
|---|---|---|---|
| 3,988,783 | A | 11/1976 | Treace |
| 4,037,592 | A | 7/1977 | Kronner |
| 4,108,165 | A | 8/1978 | Kopp et al. |
| 4,360,012 | A | 11/1982 | Mcharrie et al. |
| 4,653,487 | A | 3/1987 | Maale |
| 4,781,182 | A | 11/1988 | Purnell et al. |
| 4,815,454 | A * | 3/1989 | Dozier, Jr. ......... A61B 17/8808 606/94 |
| 4,834,757 | A | 5/1989 | Brantigan |
| 4,883,048 | A | 11/1989 | Purnell et al. |
| 4,911,153 | A | 3/1990 | Border |
| 4,920,958 | A | 5/1990 | Walt et al. |
| 4,964,861 | A | 10/1990 | Agee et al. |
| 5,098,383 | A | 3/1992 | Hemmy et al. |
| 5,163,940 | A | 11/1992 | Bourque |
| 5,178,164 | A | 1/1993 | Allen |
| 5,247,934 | A | 9/1993 | Wehrli et al. |
| 5,298,254 | A | 3/1994 | Prewett et al. |
| 5,324,295 | A | 6/1994 | Shapiro |
| 5,342,363 | A | 8/1994 | Richelsoph |
| 5,370,646 | A | 12/1994 | Reese et al. |
| 5,439,684 | A | 8/1995 | Prewett et al. |
| 5,458,602 | A | 10/1995 | Goble et al. |
| 5,514,137 | A | 5/1996 | Coutts |
| 5,556,429 | A | 9/1996 | Felt |
| 5,595,193 | A | 1/1997 | Walus et al. |
| 5,609,636 | A | 3/1997 | Kohrs et al. |
| 5,618,549 | A | 4/1997 | Patat et al. |
| 5,681,320 | A | 10/1997 | McGuire |
| 5,741,266 | A | 4/1998 | Moran et al. |
| 5,743,916 | A | 4/1998 | Greenberg et al. |
| 5,755,809 | A | 5/1998 | Cohen et al. |
| 5,766,221 | A | 6/1998 | Benderev et al. |
| 5,827,289 | A | 10/1998 | Reiley et al. |
| 5,868,749 | A | 2/1999 | Reed |
| 5,888,220 | A | 3/1999 | Felt et al. |
| 5,891,150 | A | 4/1999 | Chan |
| 5,928,239 | A | 7/1999 | Mirza |
| 5,968,047 | A | 10/1999 | Reed |
| 5,968,050 | A | 10/1999 | Torrie |
| 5,972,015 | A | 10/1999 | Scribner et al. |
| 6,010,502 | A | 1/2000 | Bagby |
| 6,019,776 | A * | 2/2000 | Preissman ......... A61B 17/3472 600/567 |
| 6,036,696 | A | 3/2000 | Lambrecht et al. |
| 6,039,742 | A | 3/2000 | Krettek et al. |
| 6,048,346 | A | 4/2000 | Reiley et al. |
| 6,066,154 | A | 5/2000 | Reiley et al. |
| 6,110,211 | A | 8/2000 | Weiss |
| 6,111,164 | A | 8/2000 | Rainey et al. |
| 6,120,511 | A | 9/2000 | Chan |
| 6,140,452 | A | 10/2000 | Felt et al. |
| 6,143,030 | A | 11/2000 | Schroder |
| 6,162,225 | A | 12/2000 | Gertzman et al. |
| 6,214,013 | B1 | 4/2001 | Lambrecht et al. |
| 6,235,043 | B1 | 5/2001 | Reiley et al. |
| 6,241,734 | B1 * | 6/2001 | Scribner ............ A61B 17/8816 606/93 |
| 6,248,110 | B1 | 6/2001 | Reiley et al. |
| 6,248,131 | B1 | 6/2001 | Felt et al. |
| 6,254,605 | B1 | 7/2001 | Howell |
| 6,267,770 | B1 | 7/2001 | Truwit |
| 6,270,528 | B1 | 8/2001 | Mckay |
| 6,283,942 | B1 | 9/2001 | Staehlin et al. |
| 6,285,901 | B1 | 9/2001 | Taicher et al. |
| 6,287,313 | B1 | 9/2001 | Sasso |
| 6,294,187 | B1 | 9/2001 | Boyce et al. |
| 6,306,177 | B1 | 10/2001 | Felt et al. |
| 6,342,056 | B1 | 1/2002 | Mac-Thiong et al. |
| 6,358,251 | B1 | 3/2002 | Mirza |
| 6,368,322 | B1 | 4/2002 | Luks et al. |
| 6,395,007 | B1 | 5/2002 | Bhatnagar et al. |
| 6,398,811 | B1 | 6/2002 | Mckay |
| 6,423,083 | B2 | 7/2002 | Reiley et al. |
| 6,486,232 | B1 | 11/2002 | Wise et al. |
| 6,506,192 | B1 | 1/2003 | Gertzman et al. |
| 6,506,785 | B2 | 1/2003 | Evans et al. |
| 6,520,969 | B2 | 2/2003 | Lambrecht et al. |
| 6,527,773 | B1 | 3/2003 | Lin et al. |
| 6,533,794 | B2 | 3/2003 | Chakeres |
| 6,564,083 | B2 | 5/2003 | Stevens |
| 6,607,561 | B2 | 8/2003 | Brannon |
| 6,613,054 | B2 | 9/2003 | Scribner et al. |
| 6,645,213 | B2 | 11/2003 | Sand et al. |
| 6,663,647 | B2 | 12/2003 | Reiley et al. |
| 6,719,761 | B1 | 4/2004 | Reiley et al. |
| 6,726,691 | B2 | 4/2004 | Osorio et al. |
| 6,730,124 | B2 | 5/2004 | Steiner |
| 6,746,451 | B2 | 6/2004 | Middleton et al. |
| 6,767,369 | B2 | 7/2004 | Boyer, II et al. |
| 6,814,736 | B2 | 11/2004 | Reiley et al. |
| 6,827,720 | B2 | 12/2004 | Leali |
| 6,863,672 | B2 | 3/2005 | Reiley et al. |
| 6,863,899 | B2 | 3/2005 | Koblish et al. |
| 6,869,434 | B2 | 3/2005 | Choi |
| 6,875,212 | B2 | 4/2005 | Shaolian et al. |
| 6,887,246 | B2 | 5/2005 | Bhatnagar et al. |
| 6,899,719 | B2 | 5/2005 | Reiley et al. |
| 6,917,827 | B2 | 7/2005 | Kienzle, III |
| 6,918,916 | B2 | 7/2005 | Gobel et al. |
| 6,923,813 | B2 | 8/2005 | Phillips et al. |
| 6,979,341 | B2 | 12/2005 | Scribner et al. |
| 6,981,981 | B2 | 1/2006 | Reiley |
| 7,001,431 | B2 | 2/2006 | Bao |
| 7,029,477 | B2 | 4/2006 | Grimm |
| 7,063,701 | B2 | 6/2006 | Michelson |
| 7,063,702 | B2 | 6/2006 | Michelson |
| 7,087,082 | B2 | 8/2006 | Paul et al. |
| 7,094,239 | B1 | 8/2006 | Michelson |
| 7,115,146 | B2 | 10/2006 | Boyer, II et al. |
| 7,144,414 | B2 | 12/2006 | Harvie et al. |
| 7,153,305 | B2 | 12/2006 | Johnson et al. |
| 7,153,306 | B2 | 12/2006 | Ralph et al. |
| 7,153,307 | B2 | 12/2006 | Scribner et al. |
| 7,155,306 | B2 | 12/2006 | Haitin et al. |
| 7,160,305 | B2 | 1/2007 | Schmieding |
| 7,192,431 | B2 | 3/2007 | Hangody et al. |
| 7,226,481 | B2 | 6/2007 | Kuslich |
| 7,241,303 | B2 | 7/2007 | Reiss et al. |

(56) References Cited

U.S. PATENT DOCUMENTS

| | | |
|---|---|---|
| 7,250,055 B1 | 7/2007 | Vanderwalle |
| 7,252,671 B2 | 8/2007 | Scribner et al. |
| 7,261,716 B2 | 8/2007 | Strobel et al. |
| 7,261,720 B2 | 8/2007 | Stevens et al. |
| 7,313,430 B2 | 12/2007 | Urquhart et al. |
| 7,399,306 B2 | 7/2008 | Reiley et al. |
| 7,410,947 B2 | 8/2008 | Rueger et al. |
| 7,448,264 B2 | 11/2008 | Boyce et al. |
| 7,458,977 B2 | 12/2008 | McGinley et al. |
| 7,468,075 B2 | 12/2008 | Lang et al. |
| 7,476,226 B2 | 1/2009 | Weikel et al. |
| 7,477,770 B2 | 1/2009 | Wehrli et al. |
| 7,485,119 B2 | 2/2009 | Thelen et al. |
| 7,488,348 B2 | 2/2009 | Truncale et al. |
| 7,491,205 B1 | 2/2009 | Michelson |
| 7,507,240 B2 | 3/2009 | Olsen |
| 7,534,226 B2 | 5/2009 | Mernoe et al. |
| 7,545,964 B2 | 6/2009 | Lang et al. |
| 7,550,007 B2 | 6/2009 | Malinin |
| 7,550,011 B2 | 6/2009 | Mckay et al. |
| 7,556,295 B2 | 7/2009 | Holzheu |
| 7,559,932 B2 | 7/2009 | Truckai et al. |
| 7,575,578 B2 | 8/2009 | Wetzler et al. |
| 7,594,917 B2 | 9/2009 | Whittaker et al. |
| 7,608,097 B2 | 10/2009 | Kyle |
| 7,608,098 B1 | 10/2009 | Stone |
| 7,643,664 B2 | 1/2010 | Wehrli et al. |
| 7,682,378 B2 | 3/2010 | Truckai et al. |
| 7,704,256 B2 | 4/2010 | Sand et al. |
| 7,708,742 B2 | 5/2010 | Scribner et al. |
| 7,713,273 B2 | 5/2010 | Krueer et al. |
| 7,731,720 B2 | 6/2010 | Sand et al. |
| 7,753,963 B2 | 7/2010 | Boyer, II et al. |
| 7,769,213 B2 | 8/2010 | Gregory et al. |
| 7,771,431 B2 | 8/2010 | Scribner et al. |
| 7,789,912 B2 | 9/2010 | Manzi et al. |
| 7,811,290 B2 | 10/2010 | Rabiner |
| 7,837,733 B2 | 11/2010 | Collins et al. |
| 7,837,740 B2 | 11/2010 | Semler et al. |
| 7,840,247 B2 | 11/2010 | Liew et al. |
| 7,846,206 B2 | 12/2010 | Oglaza et al. |
| 7,879,038 B2 | 2/2011 | Reiley et al. |
| 7,879,099 B2 | 2/2011 | Zipnick |
| 7,887,543 B2 | 2/2011 | Sand et al. |
| 7,887,546 B2 | 2/2011 | Gil |
| 7,896,885 B2 | 3/2011 | Miniaci et al. |
| 7,901,408 B2 | 3/2011 | Ek |
| 7,901,457 B2 | 3/2011 | Truncale et al. |
| 7,905,924 B2 | 3/2011 | White |
| 7,914,539 B2 | 3/2011 | Stone et al. |
| 7,927,339 B2 | 4/2011 | Ralph et al. |
| 7,931,840 B2 | 4/2011 | Michelson |
| 7,938,835 B2 | 5/2011 | Boucher et al. |
| 7,959,638 B2 | 6/2011 | Osorio et al. |
| 7,985,231 B2 | 7/2011 | Sankaran |
| 8,029,511 B2 | 10/2011 | Bowman et al. |
| 8,062,364 B1 | 11/2011 | Sharkey et al. |
| 8,070,753 B2 | 12/2011 | Truckai et al. |
| 8,092,480 B2 | 1/2012 | Layne |
| 8,133,226 B2 | 3/2012 | Chou et al. |
| 8,142,462 B2 | 3/2012 | Middleton |
| 8,152,813 B2 | 4/2012 | Osorio et al. |
| 8,168,692 B2 | 5/2012 | Wenz |
| 8,187,327 B2 | 5/2012 | Edidin et al. |
| 8,246,681 B2 | 8/2012 | Osorio et al. |
| 8,608,802 B2 | 12/2013 | Bagga et al. |
| 8,617,166 B2 | 12/2013 | Hanson et al. |
| 8,617,176 B2 | 12/2013 | Lizardi et al. |
| 8,636,745 B2 | 1/2014 | Almutairi et al. |
| 8,801,800 B2 | 8/2014 | Bagga et al. |
| 8,821,504 B2 | 9/2014 | Sharkey et al. |
| 8,864,768 B2 | 10/2014 | Hanson et al. |
| 8,906,032 B2 | 12/2014 | Hanson et al. |
| 8,951,261 B2 | 2/2015 | Sharkey et al. |
| 9,033,987 B2 | 5/2015 | Hanson et al. |
| 9,119,721 B2 | 9/2015 | Sharkey et al. |
| 9,259,257 B2 | 2/2016 | Bagga et al. |
| 9,271,835 B2 | 3/2016 | Bagga |
| 9,351,746 B2 | 5/2016 | Hanson et al. |
| 9,351,835 B2 | 5/2016 | Sharkey et al. |
| 9,386,996 B2 | 7/2016 | Hanson et al. |
| 9,439,765 B2 | 9/2016 | Bagga et al. |
| 2002/0029084 A1 | 3/2002 | Paul et al. |
| 2002/0032447 A1* | 3/2002 | Weikel ............... A61B 17/1671 606/86 R |
| 2002/0049449 A1* | 4/2002 | Bhatnagar .......... A61B 17/3472 606/94 |
| 2002/0151897 A1 | 10/2002 | Zirkle, Jr. |
| 2003/0009235 A1 | 1/2003 | Manrique et al. |
| 2003/0097135 A1 | 5/2003 | Penenberg |
| 2003/0105468 A1 | 6/2003 | Gorek |
| 2003/0120344 A1 | 6/2003 | Michelson |
| 2003/0138473 A1 | 7/2003 | Koblish et al. |
| 2003/0220651 A1 | 11/2003 | Pusnik et al. |
| 2003/0225456 A1 | 12/2003 | Ek |
| 2004/0002713 A1* | 1/2004 | Olson, Jr. .......... A61B 17/7098 606/93 |
| 2004/0002759 A1 | 1/2004 | Ferree |
| 2004/0010261 A1 | 1/2004 | Hoag et al. |
| 2004/0106925 A1 | 6/2004 | Culbert |
| 2004/0127987 A1 | 7/2004 | Evans et al. |
| 2004/0167538 A1 | 8/2004 | Gerber et al. |
| 2005/0075641 A1 | 4/2005 | Singhatat et al. |
| 2005/0119219 A1 | 6/2005 | Bellini et al. |
| 2005/0119753 A1 | 6/2005 | Mcgahan et al. |
| 2005/0149022 A1 | 7/2005 | Shaolian et al. |
| 2005/0159812 A1 | 7/2005 | Dinger, III et al. |
| 2005/0177171 A1 | 8/2005 | Wetzler et al. |
| 2005/0182418 A1 | 8/2005 | Boyd et al. |
| 2005/0203622 A1 | 9/2005 | Steiner et al. |
| 2005/0203623 A1 | 9/2005 | Steiner et al. |
| 2005/0256527 A1 | 11/2005 | Delfosse et al. |
| 2005/0267584 A1 | 12/2005 | Burdulis, Jr. et al. |
| 2005/0288795 A1 | 12/2005 | Bagga et al. |
| 2006/0052791 A1 | 3/2006 | Hagen et al. |
| 2006/0064164 A1 | 3/2006 | Thelen et al. |
| 2006/0084986 A1 | 4/2006 | Grinberg et al. |
| 2006/0247642 A1 | 11/2006 | Stone et al. |
| 2006/0271059 A1 | 11/2006 | Reay-Young et al. |
| 2007/0055280 A1 | 3/2007 | Osorio et al. |
| 2007/0093834 A1* | 4/2007 | Stevens ............... A61B 17/0401 606/279 |
| 2007/0100462 A1 | 5/2007 | Lang et al. |
| 2007/0127987 A1 | 6/2007 | Altenbuchner |
| 2007/0225813 A1 | 9/2007 | Haines |
| 2007/0276370 A1 | 11/2007 | Altarac et al. |
| 2007/0282346 A1 | 12/2007 | Scribner et al. |
| 2008/0027434 A1 | 1/2008 | Zucherman et al. |
| 2008/0039857 A1 | 2/2008 | Giersch et al. |
| 2008/0039866 A1 | 2/2008 | Stetz et al. |
| 2008/0077251 A1 | 3/2008 | Chen et al. |
| 2008/0103506 A1 | 5/2008 | Volpi et al. |
| 2008/0195115 A1 | 8/2008 | Oren et al. |
| 2008/0243127 A1 | 10/2008 | Lang et al. |
| 2008/0281331 A1 | 11/2008 | Fritzinger et al. |
| 2008/0288006 A1 | 11/2008 | Brannon |
| 2008/0306490 A1 | 12/2008 | Lakin et al. |
| 2009/0062797 A1 | 3/2009 | Huebner et al. |
| 2009/0069901 A1 | 3/2009 | Truncale et al. |
| 2009/0093813 A1 | 4/2009 | Elghazaly et al. |
| 2009/0204158 A1 | 8/2009 | Sweeney |
| 2010/0015202 A1 | 1/2010 | Semler et al. |
| 2010/0076503 A1 | 3/2010 | Beyar et al. |
| 2010/0145451 A1 | 6/2010 | Dee |
| 2010/0160970 A1 | 6/2010 | Sevrain |
| 2010/0179549 A1 | 7/2010 | Keller et al. |
| 2010/0274254 A1 | 10/2010 | Boileau et al. |
| 2011/0125156 A1 | 5/2011 | Sharkey et al. |
| 2011/0125157 A1 | 5/2011 | Sharkey et al. |
| 2011/0125159 A1 | 5/2011 | Hanson et al. |
| 2011/0125160 A1 | 5/2011 | Bagga et al. |
| 2011/0125200 A1 | 5/2011 | Hanson et al. |
| 2011/0125201 A1 | 5/2011 | Hanson et al. |
| 2011/0125264 A1 | 5/2011 | Bagga et al. |

(56) References Cited

U.S. PATENT DOCUMENTS

| | | |
|---|---|---|
| 2011/0125265 A1 | 5/2011 | Bagga et al. |
| 2011/0125272 A1 | 5/2011 | Bagga et al. |
| 2014/0074103 A1 | 3/2014 | Mandeen et al. |
| 2014/0107781 A1 | 4/2014 | Bagga et al. |
| 2014/0114369 A1 | 4/2014 | Hanson et al. |
| 2014/0350683 A1 | 11/2014 | Sharkey et al. |
| 2014/0350685 A1 | 11/2014 | Bagga et al. |
| 2015/0025589 A1 | 1/2015 | Hanson et al. |
| 2015/0230807 A1 | 8/2015 | Hanson et al. |
| 2015/0257886 A1 | 9/2015 | Sharkey et al. |
| 2016/0270834 A1 | 9/2016 | Sharkey et al. |

FOREIGN PATENT DOCUMENTS

| | | | |
|---|---|---|---|
| CN | 101460105 A | 6/2009 | |
| CN | 102770067 A | 11/2012 | |
| CN | 102781348 A | 11/2012 | |
| CN | 102740784 B | 9/2015 | |
| DK | WO 8903695 A1 * | 5/1989 | ......... A61B 17/8802 |
| EP | 2501303 A1 | 9/2012 | |
| EP | 2501306 A1 | 9/2012 | |
| EP | 2501314 A1 | 9/2012 | |
| EP | 2501342 A1 | 9/2012 | |
| WO | WO-03084412 A1 | 10/2003 | |
| WO | WO-2005079881 A1 | 9/2005 | |
| WO | WO-2008155772 A1 | 12/2008 | |
| WO | WO-2011063240 A1 | 5/2011 | |
| WO | WO-2011063250 A1 | 5/2011 | |
| WO | WO-2011063257 A1 | 5/2011 | |
| WO | WO-2011063267 A1 | 5/2011 | |
| WO | WO-2011063279 A1 | 5/2011 | |
| WO | WO-2011063281 A1 | 5/2011 | |

OTHER PUBLICATIONS

U.S. Appl. No. 12/950,230, Response filed Jul. 15, 2015 to Non Final Office Action mailed Apr. 15, 2015, 16 pgs.

U.S. Appl. No. 12/950,273, Final Office Action mailed Mar. 14, 2016, 13 pgs.

U.S. Appl. No. 12/950,273, Non Final Office Action mailed Nov. 24, 2015, 10 pgs.

U.S. Appl. No. 12/950,273, Response Dec. 29, 2015 to Non Final Office Action mailed Nov. 24, 2015, 11 pgs.

U.S. Appl. No. 14/109,368, Final Office Action mailed Jul. 9, 2015, 10 pgs.

U.S. Appl. No. 14/109,368, Notice of Allowance mailed Nov. 24, 2015, 10 pgs.

U.S. Appl. No. 14/109,368, Response filed Nov. 9, 2015 to Final Office Action mailed Jul. 9, 2015, 17 pgs.

U.S. Appl. No. 14/453,301, Final Office Action mailed Mar. 28, 2016, 11 pgs.

U.S. Appl. No. 14/453,301, Non Final Office Action mailed Sep. 23, 2015, 17 pgs.

U.S. Appl. No. 14/453,301, Notice of Allowance mailed Jun. 17, 2016, 8 pgs.

U.S. Appl. No. 14/453,301, Response filed May 31, 2016 to Final Office Action mailed Mar. 28, 2016, 11 pgs.

U.S. Appl. No. 14/453,301, Response filed Dec. 23, 2015 to Non Final Office Action mailed Sep. 23, 2015, 15 pgs.

U.S. Appl. No. 14/454,298, Notice of Allowance mailed Jul. 1, 2015, 6 pgs.

U.S. Appl. No. 14/508,436, Non Final Office Action mailed Sep. 11, 2015, 7 pgs.

U.S. Appl. No. 14/508,436, Notice of Allowance mailed Feb. 4, 2016, 5 pgs.

U.S. Appl. No. 14/508,436, Response filed Dec. 11, 2015 to Non Final Office Action mailed Sep. 11, 2015, 10 pgs.

U.S. Appl. No. 14/695,516, Non Final Office Action mailed Dec. 18, 2015, 8 pgs.

U.S. Appl. No. 14/695,516, Notice of Allowability mailed May 26, 2016, 2 pgs.

U.S. Appl. No. 14/695,516, Notice of Allowance mailed Apr. 28, 2016, 5 pgs.

U.S. Appl. No. 14/695,516, Response filed Mar. 14, 2016 to Non-Final Office Action mailed Dec. 18, 2015, 10 pgs.

U.S. Appl. No. 14/724,160, Non Final Office Action mailed Sep. 11, 2015, 5 pgs.

U.S. Appl. No. 14/724,160, Notice of Allowance mailed Feb. 4, 2016, 5 pgs.

U.S. Appl. No. 14/724,160, Preliminary Amendment filed Jun. 17, 2015, 8 pgs.

U.S. Appl. No. 14/724,160, Response filed Nov. 25, 2015 to Non Final Office Action mailed Sep. 11, 2015, 8 pgs.

U.S. Appl. No. 15/166,345, Preliminary Amendment filed Jun. 1, 2016, 7 pgs.

U.S. Appl. No. 12/950,061, Final Office Action mailed Jul. 15, 2013, 7 pgs.

U.S. Appl. No. 12/950,061, Non Final Office Action mailed Feb. 7, 2013, 7 pgs.

U.S. Appl. No. 12/950,061, Notice of Allowance mailed Oct. 1, 2013, 6 pgs.

U.S. Appl. No. 12/950,061, Preliminary Amendment filed Feb. 8, 2011, 3 pgs.

U.S. Appl. No. 12/950,061, Response filed Jun. 7, 2013 to Non Final Office Action mailed Feb. 7, 2013, 14 pgs.

U.S. Appl. No. 12/950,061, Response filed Sep. 16, 2013 to Final Office Action mailed Jul. 15, 2013, 13 pgs.

U.S. Appl. No. 12/950,097, Final Office Action mailed Dec. 10, 2013, 6 pgs.

U.S. Appl. No. 12/950,097, Non Final Office Action mailed Feb. 15, 2013, 8 pgs.

U.S. Appl. No. 12/950,097, Non Final Office Action mailed Aug. 6, 2013, 6 pgs.

U.S. Appl. No. 12/950,097, Notice of Allowance mailed Apr. 2, 2014, 5 pgs.

U.S. Appl. No. 12/950,097, Notice of Allowance mailed Jul. 9, 2014, 5 pgs.

U.S. Appl. No. 12/950,097, Preliminary Amendment filed Feb. 7, 2011, 3 pgs.

U.S. Appl. No. 12/950,097, Response filed Mar. 10, 2014 to Final Office Action mailed Dec. 10, 2013, 13 pgs.

U.S. Appl. No. 12/950,097, Response filed Jun. 17, 2013 to Non Final Office Action mailed Feb. 15, 2013, 15 pgs.

U.S. Appl. No. 12/950,097, Response filed Nov. 6, 2013 to Non Final Office Action mailed Aug. 6, 2013, 14 pgs.

U.S. Appl. No. 12/950,114, Final Office Action mailed Jul. 15, 2013, 6 pgs.

U.S. Appl. No. 12/950,114, Non Final Office Action mailed Feb. 6, 2014, 6 pgs.

U.S. Appl. No. 12/950,114, Non Final Office Action mailed Mar. 7, 2013, 6 pgs.

U.S. Appl. No. 12/950,114, Notice of Allowance mailed Jun. 16, 2014, 5 pgs.

U.S. Appl. No. 12/950,114, Preliminary Amendment filed Feb. 8, 2011, 3 pgs.

U.S. Appl. No. 12/950,114, Response filed May 6, 2014 to Non-Final Office Action mailed Feb. 6, 2014, 7 pgs.

U.S. Appl. No. 12/950,114, Response filed Jun. 7, 2013 to Non Final Office Action mailed Mar. 7, 2013, 8 pgs.

U.S. Appl. No. 12/950,114, Response filed Sep. 16, 2013 to Final Office Action mailed Jul. 15, 2013, 8 pgs.

U.S. Appl. No. 12/950,154, Examiner Interview Summary mailed Aug. 19, 2014, 3 pgs.

U.S. Appl. No. 12/950,154, Final Office Action mailed Aug. 8, 2014, 7 pgs.

U.S. Appl. No. 12/950,154, Non Final Office Action mailed Feb. 25, 2014, 6 pgs.

U.S. Appl. No. 12/950,154, Non Final Office Action mailed Mar. 15, 2013, 8 pgs.

U.S. Appl. No. 12/950,154, Notice of Allowance mailed Oct. 10, 2014, 6 pgs.

(56) References Cited

OTHER PUBLICATIONS

U.S. Appl. No. 12/950,154, Preliminary Amendment filed Feb. 7, 2011, 4 pgs.
U.S. Appl. No. 12/950,154, Response filed Jun. 17, 2013 to Non Final Office Action mailed Mar. 15, 2013, 15 pgs.
U.S. Appl. No. 12/950,154, Response filed Aug. 25, 2014 to Non-Final Office Action mailed Feb. 25, 2014, 18 pgs.
U.S. Appl. No. 12/950,154, Response filed Oct. 8, 2013 to Final Office Action mailed Aug. 8, 2013, 18 pgs.
U.S. Appl. No. 12/950,183, Examiner Interview Summary mailed Feb. 13, 2014, 3 pgs.
U.S. Appl. No. 12/950,183, Final Office Action mailed Oct. 30, 2012, 16 pgs.
U.S. Appl. No. 12/950,183, Non Final Office Action mailed May 29, 2012, 10 pgs.
U.S. Appl. No. 12/950,183, Non Final Office Action mailed Oct. 11, 2013, 12 pgs.
U.S. Appl. No. 12/950,183, Notice of Allowance mailed Feb. 19, 2014, 5 pgs.
U.S. Appl. No. 12/950,183, Notice of Allowance mailed Jun. 6, 2014, 7 pgs.
U.S. Appl. No. 12/950,183, Preliminary Amendment filed Feb. 8, 2011, 4 pgs.
U.S. Appl. No. 12/950,183, Response filed Jan. 13, 2014 to Non Final Office Action mailed Oct. 11, 2013, 11 pgs.
U.S. Appl. No. 12/950,183, Response filed Apr. 30, 2013 to Final Office Action mailed Oct. 30, 2012, 11 pgs.
U.S. Appl. No. 12/950,183, Response filed May 11, 2012 to Restriction Requirement mailed Apr. 13, 2013, 2 pgs.
U.S. Appl. No. 12/950,183, Response filed Aug. 28, 2012 to Non Final Office Action mailed May 29, 2012, 10 pgs.
U.S. Appl. No. 12/950,183, Restriction Requirement mailed Apr. 13, 2012, 8 pgs.
U.S. Appl. No. 12/950,183, Supplemental Amendment filed Feb. 7, 2014, 8 pgs.
U.S. Appl. No. 12/950,230, Final Office Action mailed Jan. 11, 2013, 10 pgs.
U.S. Appl. No. 12/950,230, Non Final Office Action mailed Jul. 17, 2014, 10 pgs.
U.S. Appl. No. 12/950,230, Non Final Office Action mailed Aug. 2, 2012, 9 pgs.
U.S. Appl. No. 12/950,230, Preliminary Amendment filed Feb. 8, 2011, 3 pgs.
U.S. Appl. No. 12/950,230, Response filed Apr. 11, 2013 to Final Office Action mailed Jan. 11, 2013, 10 pgs.
U.S. Appl. No. 12/950,273, Final Office Action mailed Nov. 6, 2012, 9 pgs.
U.S. Appl. No. 12/950,273, Non Final Office Action mailed Apr. 13, 2012, 15 pgs.
U.S. Appl. No. 12/950,273, Non Final Office Action mailed Apr. 25, 2014, 12 pgs.
U.S. Appl. No. 12/950,273, Preliminary Amendment filed Feb. 8, 2011, 3 pgs.
U.S. Appl. No. 12/950,273, Response filed Mar. 6, 2013 to Final Office Action mailed Nov. 6, 2012, 10 pgs.
U.S. Appl. No. 12/950,273, Response filed Jul. 12, 2012 to Non Final Office Action mailed Apr. 13, 2012, 12 pgs.
U.S. Appl. No. 12/950,273, Response filed Oct. 24, 2014 to Non-Final Office Action mailed Apr. 24, 2014, 14 pgs.
U.S. Appl. No. 12/950,306, Final Office Action mailed Nov. 26, 2012, 9 pgs.
U.S. Appl. No. 12/950,306, Non Final Office Action mailed Jun. 14, 2012, 11 pgs.
U.S. Appl. No. 12/950,306, Notice of Allowance mailed May 28, 2013, 9 pgs.
U.S. Appl. No. 12/950,306, Notice of Allowance mailed Aug. 13, 2013, 9 pgs.
U.S. Appl. No. 12/950,306, Preliminary Amendment filed Feb. 8, 2011, 7 pgs.
U.S. Appl. No. 12/950,306, Response filed Apr. 3, 2013 to Final Office Action mailed Nov. 26, 2012, 15 pgs.
U.S. Appl. No. 12/950,306, Response filed Sep. 13, 2012 to Non Final Office Action mailed Jun. 14, 2012, 11 pgs.
U.S. Appl. No. 12/950,355, Final Office Action mailed Mar. 12, 2013, 15 pgs.
U.S. Appl. No. 12/950,355, Non Final Office Action mailed Jul. 29, 2014, 9 pgs.
U.S. Appl. No. 12/950,355, Non Final Office Action mailed Aug. 13, 2012, 16 pgs.
U.S. Appl. No. 12/950,355, Notice of Allowance mailed Dec. 9, 2014, 6 pgs.
U.S. Appl. No. 12/950,355, Response filed Jan. 14, 2013 Non Final Office Action mailed Aug. 13, 2012, 17 pgs.
U.S. Appl. No. 12/950,355, Response filed Jul. 12, 2013 to Final Office Action mailed Mar. 12, 2013, 20 pgs.
U.S. Appl. No. 12/950,355, Response filed Oct. 28, 2014 to Non-Final Office Action mailed Jul. 29, 2014, 21 pgs.
U.S. Appl. No. 14/143,883, Non Final Office Action mailed Aug. 4, 2014, 6 pgs.
U.S. Appl. No. 14/453,301, Preliminary Amendment filed Oct. 6, 2014, 8 pgs.
U.S. Appl. No. 14/454,298, Preliminary Amendment filed Sep. 18, 2014, 7 pgs.
"Chinese Application Serial No. 201080020717.2, Office Action mailed Jan. 9, 2014", (W/English Translation), 11 pgs.
"Chinese Application Serial No. 201080052569.2, Office Action mailed Apr. 25, 2014", (W/English Translation), 17 pgs.
"Chinese Application Serial No. 201080052578.1, Office Action mailed Apr. 1, 2014", (w/English Translation), 11 pgs.
"Chinese Application Serial No. 201080052580.9, Office Action mailed Apr. 3, 2014", (w/English Translation), 18 pgs.
"Chinese Application Serial No. 201080052583.2, Office Action mailed Mar. 14, 2014", (w/English Translation), 9 pgs.
"European Application Serial No. 10832277.7, Office Action mailed Jun. 27, 2012", 2 pgs.
"European Application Serial No. 10832285.0, Office Action mailed Jun. 27, 2012", 2 pgs.
"International Application Serial No. PCT/US2010/057426, International Preliminary Report on Patentability mailed May 22, 2012", 9 pgs.
"International Application Serial No. PCT/US2010/057426, International Search Report and Written Opinion mailed Jan. 24, 2011", 10 pgs.
"International Application Serial No. PCT/US2010/057440, International Preliminary Report on Patentability mailed May 22, 2012", 7 pgs.
"International Application Serial No. PCT/US2010/057440, International Search Report and Written Opinion mailed Feb. 7, 2011", 8 pgs.
"International Application Serial No. PCT/US2010/057456, International Preliminary Report on Patentability mailed May 22, 2012", 6 pgs.
"International Application Serial No. PCT/US2010/057456, International Search Report and Written Opinion mailed Jan. 14, 2011", 7 pgs.
"International Application Serial No. PCT/US2010/057471, International Preliminary Report on Patentability mailed May 31, 2012", 7 pgs.
"International Application Serial No. PCT/US2010/057471, International Search Report mailed Jan. 18, 2011", 2 pgs.
"International Application Serial No. PCT/US2010/057471, Written Opinion mailed Jan. 18, 2011", 5 pgs.
"International Application Serial No. PCT/US2010/057475, International Preliminary Report on Patentability mailed May 22, 2012", 6 pgs.
"International Application Serial No. PCT/US2010/057475, International Search Report mailed Jan. 18, 2011", 8 pgs.
"International Application Serial No. PCT/US2010/057475, Written Opinion mailed Jan. 18, 2011", 5 pgs.
"International Application Serial No. PCT/US2010/057483, International Preliminary Report on Patentability mailed May 22, 2012", 6 pgs.

(56) References Cited

OTHER PUBLICATIONS

"International Application Serial No. PCT/US2010/057483, International Search Report and Written Opinion mailed Feb. 2, 2011", 7 pgs.
"International Application Serial No. PCT/US2010/057498, International Preliminary Report on Patentability mailed May 22, 2012", 5 pgs.
"International Application Serial No. PCT/US2010/057498, International Search Report mailed Jan. 24, 2011", 2 pgs.
"International Application Serial No. PCT/US2010/057498, Written Opinion mailed Jan. 24, 2011", 4 pgs.
"International Application Serial No. PCT/US2010/057500, International Preliminary Report on Patentability mailed May 31, 2012", 8 pgs.
"International Application Serial No. PCT/US2010/057500, International Search Report mailed Jan. 27, 2011", 2 pgs.
"International Application Serial No. PCT/US2010/057500, Written Opinion mailed Jan. 27, 2011", 6 pgs.
"Riddle Memorial Hospital, Medial, PA 19063 Operative Report. Surgeon: Peter F Sharkey M.D.", Right Knee, Medial tibial plateau; A cannulated bone biopsy needle was placed into the bone under fluoroscopic guidance;, Implant used: Stryker Orthopedics Hydroset (Bone Substitute Material); Surgeon also expressed difficulty in injecting the bone substitute, (May 12, 2008), 2 pgs.
"SPU Operative Report. Surgen: Steven B Cohen, M.D.", Treatment of the central medial tibial plateau; A guide pin was inserted into the medial tibial plateau;, An endo button drill bit was used to expand the drill hole; One cubic centimeter (cc) of cement was inserted into the bone; A second drill hole was made from below, and a second cc was inserted into the bone., (Nov. 10, 2008), 4 pgs.
"SPU Operative Report: Surgen Steven B Cohen, M.D.", An Anterior Cruciate Ligament (ACL) portal-creation device was repurposed for this surgery; The tibial probe was placed on the medial femoral condyle, with the tunnel guide secured proximally on the thigh;, The surgeon expressed difficulty in positioning and stabilizing the guide; A cannulated pin was placed through the tunnel guide and placed distally into the medial femoral condyle; No implant was injected into the bone., (Oct. 27, 2008), 4 pgs.
U.S. Appl. No. 12/950,230, Examiner Interview Summary mailed Nov. 12, 2014, 3 pgs.
U.S. Appl. No. 12/950,230, Final Office Action mailed Jan. 13, 2015, 10 pgs.
U.S. Appl. No. 12/950,230, Response filed Nov. 2, 2012 to Non Final Office Action mailed Aug. 2, 2012, 8 pgs.
U.S. Appl. No. 12/950,230, Response filed Nov. 17, 2014 to Non-Final Office Action mailed Jul. 17, 2014, 15 pgs.
U.S. Appl. No. 12/950,273, Final Office Action mailed Feb. 4, 2015, 28 pgs.
U.S. Appl. No. 14/143,883, Notice of Allowance mailed Jan. 26, 2015, 6 pgs.
U.S. Appl. No. 14/143,883, Response filed Dec. 4, 2014 to Non-Final Office Action mailed Aug. 4, 2014, 9 pgs.
U.S. Appl. No. 14/508,436, Preliminary Amendment filed Jan. 8, 2015, 7 pgs.
"Chinese Application Serial No. 201080052569.2 Response filed Nov. 7, 2014 to Non Final Office Action mailed Jun. 10, 2014", (W/ English Translation), 12 pgs.
"Chinese Application Serial No. 201080052578.1, Office Action mailed Dec. 17, 2014", (W/ English Translation), 4 pgs.
"Chinese Application Serial No. 201080052578.1, Response filed Jan. 22, 2015 to Office Action mailed Dec. 17, 2014", (W/ English Translation), 8 pgs.
"Chinese Application Serial No. 201080052580.9, Office Action mailed Nov. 25, 2014", (W/ English Translation), 18 pgs.
"Chinese Application Serial No. 201080052583.2, Office Action mailed Dec. 24, 2014", (W/ English Translation), 4 pgs.
"Chinese Application Serial No. 201080052583.2, Response filed Sep. 26, 2014 to Office Action mailed Mar. 14, 2014", (W/ English Translation of Claims), 10 pgs.
U.S. Appl. No. 12/950,230, Non Final Office Action mailed Apr. 15, 2015, 10 pgs.
U.S. Appl. No. 12/950,230, Response filed Mar. 24, 2015 to Final Office Action mailed Jan. 13, 2015, 11 pgs.
U.S. Appl. No. 12/950,273, Advisory Action mailed May 12, 2015, 3 pgs.
U.S. Appl. No. 12/950,273, Response filed May 4, 2015 to Final Office Action mailed Feb. 4, 2015, 14 pgs.
U.S. Appl. No. 12/950,273, Response filed Jun. 4, 2015 to Final Office Action mailed Feb. 4, 2015, 14 pgs.
U.S. Appl. No. 14/109,368, Non Final Office Action mailed Mar. 11, 2015, 6 pgs.
U.S. Appl. No. 14/109,368, Response filed May 26, 2015 to Non-Final Office Action mailed Mar. 11, 2015, 12 pgs.
U.S. Appl. No. 14/454,298, Notice of Allowance mailed Mar. 17, 2015, 8 pgs.
U.S. Appl. No. 14/695,516, Preliminary Amendment filed May 27, 2015, 6 pgs.
"Australian Application Serial No. 2010321745, Office Action mailed Jan. 12, 2015", 3 pgs.
"Australian Application Serial No. 2010321745, Response filed Apr. 24, 2015 to Office Action mailed Jan. 12, 2015", (18 pgs).
"Australian Application Serial No. 2010321812, Office Action mailed Jan. 12, 2015", 3 pgs.
"Australian Application Serial No. 2010321812, Response filed Apr. 24, 2015 to Office Action mailed Jan. 12, 2015", 19 pgs.
"Chinese Application Serial No. 201080052569.2, Office Action mailed Jan. 28, 2015", (W/ English Translation), 5 pgs.
"Chinese Application Serial No. 201080052569.2, Response filed Mar. 26, 2015 to Office Action mailed Jan. 28, 2015", W/ English Claims, 10 pgs.
"Chinese Application Serial No. 201080052578.1, Response filed Aug. 12, 2014 to Office Action mailed Apr. 1, 2014", W/ English Claims, 13 pgs.
"Chinese Application Serial No. 201080052580.9, Response filed Aug. 14, 2014 to Office Action mailed Apr. 3, 2014", W/ English Claims, 12 pgs.
U.S. Appl. No. 15/166,345, Non Final Office Action mailed Oct. 21, 2016, 6 pgs.

\* cited by examiner

SUBCHONDRAL TREATMENT OF JOINT PAIN

CROSS-REFERENCE TO RELATED APPLICATIONS

This application is a continuation of U.S. patent application Ser. No. 12/950,355, filed Nov. 19, 2010, now issued as U.S. Pat. No. 8,951,261, which claims priority to U.S. Provisional No. 61/263,170 filed Nov. 20, 2009, and entitled "METHOD FOR TREATING JOINT PAIN AND ASSOCIATED INSTRUMENTS," U.S. Provisional No. 61/292,979 filed Jan. 7, 2010, and entitled "INSTRUMENTS AND IMPLANTS FOR JOINT REPAIR AND METHODS OF USE," U.S. Provisional No. 61/300,337 filed Feb. 1, 2010, and entitled "DEVICES AND INSTRUMENTS FOR BONE REPAIR AND METHODS OF USE," U.S. Provisional No. 61/310,897 filed Mar. 5, 2010, and entitled "INSTRUMENTS FOR A VARIABLE ANGLE APPROACH TO JOINT REPAIR AND METHODS OF USE," U.S. Provisional No. 61/311,152 filed Mar. 5, 2010, and entitled "INSTRUMENTS FOR REPAIRING AN UPPER BONE OF A JOINT AND METHODS OF USE," U.S. Provisional No. 61/311,632 filed Mar. 8, 2010, and entitled "COORDINATE MAPPING SYSTEM FOR KNEE JOINT REPAIR AND METHODS OF USE," U.S. Provisional No. 61/324,931 filed Apr. 16, 2010, and entitled "IMPLANTABLE DEVICES FOR TREATING BONE DEFECTS," U.S. Provisional No. 61/354,100 filed Jun. 11, 2010, and entitled "IMPLANTABLE DEVICES AND RELATED DELIVERY TOOLS," and U.S. Provisional No. 61/337,313 filed Aug. 26, 2010, and entitled "NAVIGATION AND POSITIONING INSTRUMENTS FOR JOINT REPAIR AND METHODS OF USE," all of which are herein incorporated by reference in their entirety.

This application also relates to co-owned U.S. patent application Ser. No. 12/950,097, filed Nov. 19, 2010, now issued as U.S. Pat. No. 8,821,504,and entitled "METHOD FOR TREATING JOINT PAIN AND ASSOCIATED INSTRUMENTS," U.S. patent application Ser. No. 12/950, 306, filed Nov. 19, 2010, now issued as U.S. Pat. No. 8,608,802, and entitled "IMPLANTABLE DEVICES FOR SUBCHONDRAL TREATMENT OF JOINT PAIN," U.S. patent application Ser. No. 12/950,273, filed Nov. 19, 2010 and entitled "IMPLANTABLE DEVICES FOR SUBCHONDRAL TREATMENT OF JOINT PAIN," U.S. patent application Ser. No. 12/950,230, filed Nov. 19, 2010 and entitled "INSTRUMENTS FOR TARGETING A JOINT DEFECT," U.S. patent application Ser. No. 12/950,183, filed Nov. 19, 2010, now issued as U.S. Pat. No. 8,801,800, and entitled "BONE-DERIVED IMPLANTABLE DEVICES FOR SUBCHONDRAL TREATMENT OF JOINT PAIN," U.S. patent application Ser. No. 12/950,154, filed Nov. 19, 2010, now issued as U.S. Pat. No. 8,906,032, and entitled "INSTRUMENTS FOR VARIABLE ANGLE APPROACH TO A JOINT," U.S. patent application Ser. No. 12/950,114, filed Nov. 19, 2010, now issued as U.S. Pat. No. 8,864,768, and entitled "COORDINATE MAPPING SYSTEM FOR JOINT TREATMENT," and U.S. patent application Ser. No. 12/950,061, filed Nov. 19, 2010, now issued as U.S. Pat. No. 8,617,166, and entitled "NAVIGATION AND POSITIONING INSTRUMENTS FOR JOINT REPAIR," the contents of which are herein incorporated in their entirety by reference.

FIELD

The present invention relates to devices and instruments for the surgical treatment of bone tissue at or near a joint, and more particularly to devices, instruments and associated methods for the subchondral treatment of a defect at or near a joint.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in the knee, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

SUMMARY

The present disclosure provides devices, instruments and associated methods for the subchondral treatment of joint pain, and more specifically for the treatment of a subchondral defect at or near a joint.

In one embodiment, a kit for treating joint pain is provided. The kit comprises an implant for mechanical stabilization of a subchondral defect in a subchondral region of a bone adjacent to the joint. A delivery tool may be provided for insertion of the implant. An instrument an instrument for guiding the tool to a target location in the bone may also be provided with the kit. The instrument comprises a first portion having a first guide section configured to guide the tool to the target location. A reference probe extends from the first portion having a tip that indicates a selected landmark on the bone. A handle portion may be coupled to the first portion and having a second guide section configured to guide a tool to the target location. The first guide section is configured to guide the tool at an angle substantially parallel to the reference probe, and the second guide section is configured to guide the tool at an angle acute to the reference probe.

In another embodiment, a kit for treating joint pain is provided. The kit comprises an injectable material for biological stimulation of a healing response to a subchondral defect in a subchondral region of a bone adjacent to the joint. An injector tool can be provided with the kit for delivery of the material. The kit may also include an instrument for guiding the tool to a target location in the bone. The instrument may comprise a first portion having a first guide section configured to guide the tool to the target location. A reference probe extends from the first portion having a tip that indicates a selected landmark on the bone. A handle portion may be coupled to the first portion and having a second guide section configured to guide a tool to the target location. The first guide section is configured to guide the tool at an angle substantially parallel to the reference probe, and the second guide section is configured to guide the tool at an angle acute to the reference probe.

In yet another embodiment, a method for treating joint pain is provided. The method comprises: identifying a subchondral defect in a subchondral region of a bone of the joint; selecting a subchondral access path to a location near the subchondral defect; and treating the subchondral defect, via the subchondral access, in a manner that restores normal force distribution and joint function while preserving the articular surface of the bone.

In still another embodiment, a method for treating joint pain is provided. The method comprises: identifying a subchondral defect in a subchondral region of a bone of the joint; selecting a subchondral access path to a location near the subchondral defect; and treating the subchondral defect, via the subchondral access, by mechanically stabilizing an area in or near the subchondral defect; wherein treatment of the subchondral defect restores normal force distribution and joint function while preserving an articular surface of the bone.

In even still another embodiment, a method for treating joint pain is provided. The method comprises: identifying a subchondral defect in a subchondral region of a bone of the joint; selecting a subchondral access path to a location near the subchondral defect; and treating the subchondral defect, via the subchondral access, by stimulating healing of the bone tissue in or adjacent to the subchondral defect; wherein treatment of the subchondral defect restores normal force distribution and joint function while preserving the articular surface of the bone.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1:
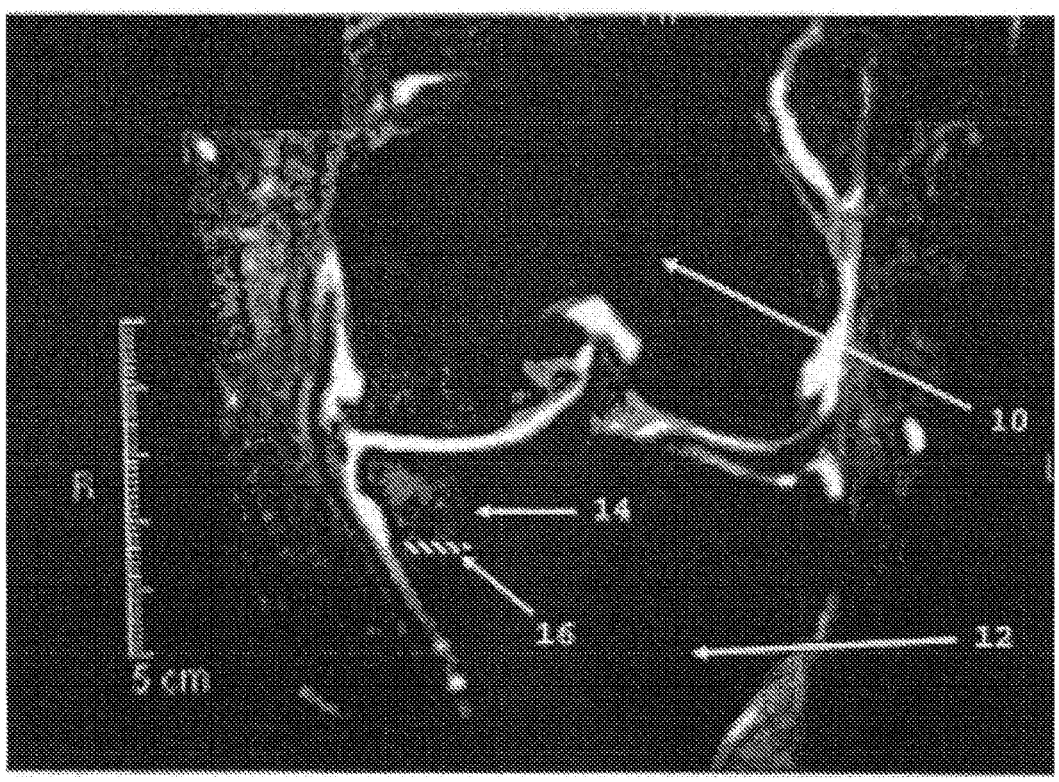
FIG. 1 is a magnetic resonance image (MRI) of an arthritic knee on which is overlaid a side view of an embodiment of the reinforcing member of the invention.

The present disclosure provides a methodology, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, the embodiments diagnose and treat pain at its source in the subchondral region of a bone of a joint to relieve the pain. Applicants have discovered that pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Applicants have discovered that treatment of the bone by mechanical and biological means to restore the normal physiologic stress distribution, and restore the healing balance of the bone tissue at the subchondral level, is a more effective way of treating pain than conventional techniques. That is, treatment can be effectively achieved by mechanically strengthening or stabilizing the defect, and biologically initiating or stimulating a healing response to the defect. Accordingly, the present disclosure provides methods, devices, and systems for a subchondral procedure. This procedure and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing which of these subchondral defects is the source of pain, and determining an extent of treatment for the subchondral defect. The present technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. The present disclosure provides several exemplary treatment modalities for SCP™ for the different extents of treatment needed. Accordingly, a medical practitioner may elect to use the techniques and devices described herein to subchondrally treat any number of bone defects as he deems appropriate.

In some embodiments, detection and identification of the relevant bone marrow lesion or bone marrow edema (BML or BME) can be achieved by imaging, e.g., magnetic resonance imaging (MRI), X-ray, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatable BML or BME may be identified as bone tissue that is chronically unable to heal (or remodel) itself versus a bone defect caused by an acute injury or trauma, which may cause a non-union of the bone, stress or insufficiency fractures, and perceptible pain. Factors considered may include, among other things, the nature of the defect, size of the defect, location of the defect, etc. For example, bone defects at the edge near the articular surface or periphery of a joint may be often considered eligible for treatment due to edge-loading effects as well as the likelihood of bone hardening at these locations.

According to the embodiments, the SCP™ treatment may continue after surgery. In particular, the patient may be monitored for a change in pain scores, positive change in function. For example, patients are also checked to see when they are able to perform full weight-bearing activity and when they can return to normal activity. Of note, if needed, the SCP™ procedure can be completely reversed in the event that a patient requires or desires a joint replacement or other type of procedure. The SCP™ treatment may also be performed in conjunction with other procedures, such as cartilage resurfacing, regeneration or replacement, if desired.

The present disclosure provides a number of treatment modalities, and associated devices, instruments and related methods of use for performing SUBCHONDROPLASTY™. These treatment modalities may be used alone or in combination.

In one treatment modality, the subchondral bone in the region of the bone marrow lesion or defect can be strengthened by introduction of a hardening material, such as a bone substitute, at the site. In some instances, some of the soft bone tissue at or near a bone marrow lesion or defect is compacted prior to insertion of the material. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion.

In another treatment modality, the subchondral bone region can be stimulated to trigger or improve the body's natural healing process. For example, in one embodiment of this treatment modality, small holes may be drilled at the region of the defect to increase stimulation (e.g., blood flow, cellular turnover, etc.) and initial bone repair. In another embodiment, after holes are drilled an osteogenic, osteoinductive, or osteoconductive agent may be introduced to the site. In addition, some of the bone tissue may be compacted in order to assist in stimulating the bone tissue or create space for the bone graft material. Bone graft material, for example, may be used to fill the hole. This treatment modality may create a better load-supporting environment leading to long term healing. Electrical or heat stimulation may also be employed to stimulate the healing process of a chronically injured bone. Chemical and bio-chemical stimulation may also be employed in SCP™. Moreover, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. In some embodiments, some of the bone tissue may be compacted at or near the bone marrow lesion or defect in order to create space for the implantable device. The implant may help create a better load distribution in the subchondral region. In the knees, the implant may support tibio-femoral compressive loads. In addition, the implant may mechanically integrate sclerotic bone with the surrounding healthy bone tissue. The implant may be placed in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Accordingly, the present disclosure also provides suitable implantable fixation devices for the surgical treatment of these altered bone regions or bone defects, especially at the subchondral level. Applicants have also discovered devices and instruments that can be used in combination with cements or hardening materials commonly used to repair damaged bone by their introduction into or near the site of damage, either to create a binding agent, cellular scaffold or mechanical scaffold for immobilization, regeneration or remodeling of the bone tissue.

As noted, embodiments of the present invention may be explained and illustrated with reference to treatment of a patient's knee, though it is understood that the devices, instruments and methods of the present invention may be applicable to other joints as well, such as the shoulder, hip and ankle. Referring now to FIG. 1, an arthritic human knee comprises a femur 10 and a tibia 12. Bone lesion 14 of tibia 12 presents as a focally increased signal in the marrow in an MRI of the knee. In certain embodiments, coronal spin-echo fat-saturated proton density, T1ρ proteoglycan and T2-weighted fat-saturated magnetic resonance images may be employed in the embodiments. In some embodiments, bone lesions, which are from 0 to 10 cm from the joint, 0 to 5 cm from the joint, or 0 to 1 cm from the joint are considered good candidates for treatment.

A bone marrow lesion 14 or other abnormality causing pain can be identified using magnetic resonance imaging (MRI), such as a T2-weighted MRI, but other identification means may be employed as well. For example, a T1-weighted MRI can be used to detect sclerotic bone (if present) associated with the bone marrow lesion 14. Another example is that a T2-weighted MRI can be used to detect lesions, edemas, and cysts. X-ray imaging may be suitable for early-stage as well as end-stage arthritis. For example, bone lesions can be identified using X-ray or Technetium-99 bone scans. In embodiments employing MRI, any MRI technology that reveals bone marrow lesions can be used, for example, open MRI, low field strength MRI, extremity MRI, whole body scanner MRI, and the like. In another embodiment, 3-dimensional imaging or image guidance technology may be employed to locate the lesion or defect. Such imaging technology would enable the lesion or defect to be located intraoperatively. Other techniques may also be used to assist identifying a source of bone, such as palpation of the join, and chemical or biological assay.

Various criteria may be employed for selecting a treatment modality and an implant in accordance with principles of the present invention. For example, a reinforcing member 16 as an implant may be selected based on a grading system that indicates various treatment modalities depending on the severity, location, and size of a bone marrow lesion or defect. Factors considered may include, among other things, the nature of the defect, size of the defect, location of the defect, etc. For example, bone defects at the edge near the articular surface or periphery of a joint may be often considered eligible for treatment due to edge-loading effects as well as the likelihood of bone hardening at these locations.

As noted, in diagnosing a patient's joint pain and selecting a treatment modality, defects that are associated with chronic injury and chronic deficit of healing are differentiated from defects that result, e.g., from diminished bone density. SCP™ treatable BML or BME may be identified as bone tissue that is chronically unable to heal (or remodel) itself versus a bone defect caused by an acute injury or trauma, which may cause a non-union of the bone, stress or insufficiency fractures, and perceptible pain.

For example, patients having a confirmed chronic marrow lesion or edema in the tibial plateau or femoral condyle may be candidates for SCP™. The length of time that a patient reports suffering pain may also be a factor in diagnosing the source of the joint pain and selecting a treatment modality. For example, patients reporting pain symptoms for at least 6 months or more may be considered suffering from a chronic condition and a good candidate for SCP™. Subjective pain perception, such as VAS scores reported by the patient, may also be considered in whether to perform SCP™ or in selecting a treatment modality. For example, VAS pain scores above 7 or 7.5 may be used as an indication considered for SCP™. Other subjective scoring systems may be used in the evaluation phase. For example, the well-known IKDC subjective score, which measures a patient's ability to perform a variety of tasks may be used as an indication. The lower the IKDC score, the more limited a patient's function. Patients reporting a pre-operative IKDC of about 35 or less may be considered good candidates for the SCP™ procedure. In addition, the SF-12 score, which is a short form of 12 questions and measures patient's overall quality of life may be requested from the patient before performing the SCP™ procedure. Patients having a SF-12 score of less than about 30 may be considered good candidates for the SCP™ procedure. Of course, if a patient is unable to perform normal daily activities, such as walking, running, or standing, then such limitations may be considered in deciding whether to perform the SCP™ and selecting a treatment modality.

In addition, the patient's physiology and other characteristics may be considered in determining the appropriate treatment modality. For example, the patient's age may be a factor, since a person's healing ability declines over age. In one embodiment, patients between the ages of 35-70 may be considered appropriate candidates for SCP™. A patient's other characteristics may be considered as well, such as their standing alignment of the patient, i.e., varus and valgus, weight, body mass index, etc.

In some embodiments, other symptoms may be considered in confirming the source of pain or need to perform a SCP™ procedure on a particular patient. For example, patients having a grade III-IV chondrosis of the relevant joint may be considered good candidates. Mechanical symptoms, such as swelling, inflammation, meniscal tearing or wear, etc., may also be confirming indications for a SCP™ procedure.

FIG. 1 shows just one example of how reinforcing member 16 could be implanted in bone lesion 14. Of course, the reinforcing member 16 may be implanted adjacent to the bone lesion 14. For example, the reinforcing member 16 can be implanted adjacent to a side of the bone lesion proximal to the joint and/or adjacent to a side of the bone lesion distal to the joint.

FIG. 1 shows one reinforcing member 16 implanted. Those skilled in the art will recognize that multiple reinforcing members can be implanted in and/or adjacent to a bone lesion according to other embodiments. In general, an implant that is 10 mm (or less) away from an outer surface of the bone lesion can be considered adjacent to that lesion. Adjacent reinforcing members can also be in contact with an outer surface of the bone lesion.

In general, the reinforcing member 16 serves to adequately distribute stresses placed on the bone. The reinforcing member 16 may be bioactive and configured to have an appropriate rigidity/flexibility and other characteristics, such as porous or non-porous coatings, as desired. In particular, the reinforcing member 16 may be sufficiently strong or stiff to make it capable of being implanted in bone and avoid stress concentration, for example, in the subchondral region of the bone. Accordingly, the reinforcing member 16 may have various dimensions and stiffness.

In some embodiments, the implant is implanted free of bonds to the bone. Thus, the reinforcing member is not, for example, glued, cemented, stapled, stitched, clamped or screwed to the bone. However, the implant may naturally or be configured to eventually bond to the bone via biological processes in situ.

In some embodiments, the reinforcing member 16 is implanted in the bone in or adjacent the bone lesion such that a proximal face faces the joint and a distal face faces away from the joint. In addition, the reinforcing member 16 may be selected or modified (e.g., cut, torn, etc.) such that a maximum dimension of the proximal face exceeds a maximum dimension of the bone lesion. It is also within the scope of the invention for the maximum dimension of the bone lesion to equal or exceed a maximum dimension of the proximal face. Thus, the reinforcing member 16 can be larger, smaller or the same size as the bone lesion.

The reinforcing member 16 can be implanted such that the proximal face is perpendicular to a longitudinal axis of the bone. In general, proximal and/or distal faces of the implant will be the primary load bearing surfaces in situ.

In certain embodiments, a syringe (optionally with a needle) can be used to inject a fluid into a bone so as to form the reinforcing member in situ. This step can be conducted with or without first creating an opening in the bone. The fluid is preferably a liquid, semi-solid, gel, hydrogel, dispersion or slurry. After injection, the fluid can remain fluid-like, or may cure to a more solid-like state. For example, the injected fluid can cross-link or polymerize from a liquid to form a semi-solid, gel or solid. Fluids that cure in situ can be self-curing or can cure in response to curing means, such as, e.g., radiation (e.g., UV light), heat (e.g., body temperature), moisture and/or a curing agent.

In other embodiments, the reinforcing member is solid in nature and may be rigid or malleable. In these embodiments, the surgeon creates a small opening in the vicinity of the bone lesion. Suitable surgical tools for this task include standard bone instruments (e.g., chisels, drills, etc.) and instruments, such as a guide/insertion instrument, designed for use in the method of the invention.

A surgeon can implant the reinforcing member 16 by studying a previously captured image of the bone marrow lesion 14 and manually estimating the location and boundaries of the bone lesion. Alternatively, a surgeon can be provided with additional guidance during surgery. For example, surgery can be conducted using real-time imaging, robotic devices, one or more braces that maintain the joint in a position consistent with captured images of the joint and/or labels, etc. Suitable labels include but are not limited to radioactive labels, such as Technetium-99 and other objects, such as fiducial markers.

Postoperatively, patients may be required to maintain partial weight bearing and use ambulatory aids. Depending upon the physician's discretion, full weight bearing may also be possible after surgery. Routine post intervention physical therapy may also be required. Patients may be treated according to routine post intervention care, observation and follow-up.

For example, patients may be evaluated approximately 7-10 days post-procedure to allow for removal of sutures, assess surgical healing, etc. According to one embodiment of SCP™, patients are allowed to have 50% weight bearing activity after about 2 weeks with crutches, followed by 1 week of progress to 100% activity. An unloader brace for about 3 months may be recommended during all weight-bearing activities lasting longer than 5 minutes. The patient may also be evaluated after about 6-8 weeks to confirm healing of fractures, non-unions, etc.

In one embodiment, the patient's subjective pain perception is measured post operatively, such as VAS for pain, IKDC, and SF-12. Ideally, a patient may be expected to report progressive or significant pain relief in their scores, better quality of life, and increasing ability to perform normal activities. Long term, patients may be monitored to confirm relief or curing of their joint pain. If needed, the SCP™ procedure may be reversed and/or supplemented with another procedure.

As noted, the SCP™ may provide various treatment modalities and employ different types of reinforcing members. The reinforcing member 16 may have various forms and shapes to maximize its surface area and reduce stress of the bone when implanted. For example, the reinforcing member 16 may be in the form of a rod having a triangular profile, a rectangular profile, or a circular profile. Reinforcing member 16 may be planar, e.g., relatively long in two dimensions and relatively short in a third dimension. Planar reinforcing members in accordance with the invention can have a thickness which is ≤50% of the length and ≤50% of the width of a rectangular reinforcing member (or ≤50% of the diameter in the case of a circular reinforcing member or ≤50% of the height and ≤50% of the base in the case of a triangular reinforcing member).

In other embodiments, the reinforcing member 16 may have a wedge-shaped edge on at least one edge or a wedge or ramp shape when viewed from the side. A wedge-shaped edge may be adapted to facilitate inserting the reinforcing member 16 into the bone. Thus, the particular angle and other dimensions of the wedge may be dictated by factors that are known in the art. As a wedge-shaped implant, the reinforcing member 16 may be similar to standard surgical tools, such as osteotomes, or comprise blade plates or osteotomy staples. Further, the reinforcing member 16 may be an expandable device that can span the defect. In one embodiment, the reinforcing member 16 may be an expandable screw, such as an osseoscrew.

In other embodiments, the reinforcing member 16 may be in the form of a closed disc, an open disc, a screw-shaped device, or an elongated pin. In addition, the reinforcing member 16 may have a square profile, rectangular profile with rounded edges, or an I-beam profile. Alternatively, the reinforcing member 16 can be an injection cement diffuser. In some embodiments, the reinforcing member 16 may be approximately 3 mm thick.

In some embodiments, the reinforcing member 16 may be customized to the patient. For example, using 3-dimensional imaging technology, it may be desirable to provide an implant that matches precisely the anatomical site where the reinforcing member 16 is to be placed. This would ensure conformability and avoid a less than perfect match between the implant and the implantation site.

The reinforcing member 16 may be porous and/or fenestrated to allow for bone ingrowth. Reinforcing member 16 comprises a physiologically compatible material that has sufficient durability to reinforce the overstressed bone of the bone lesion and bear physiologic loads. Materials for the reinforcing member 16 can include metals, such as titanium, stainless steel, alloys of cobalt and chrome, tantalum, alloys of titanium and nickel and other superelastic metal alloys. Porous titanium, titanium "foam", tantalum, trabecular metals, nanoceramics, porous nitinol, or other highly porous nanomaterials, and chrome cobalt may also be employed in the reinforcing member 16.

The reinforcing member 16 may comprise a functional coating, such as, hydroxyapatite plasma coating, titanium nitrate or bioactive glass. In addition, the reinforcing member 16 may undergo some form of surface treatment including acid etching, grit blast, or plasma spray. The reinforcing member may also comprise structural enhancements such as meshes, and include autograft. The member 16 may also be formed of, or include, porous metals like tantalum or ACTIPORE.

Other embodiments comprise the use of bone, such as autografts, allografts, and artificial or synthetic bone substitutes. Certain embodiments comprise the use of polymeric materials. A combination of materials, such as a porous metal applied to a carbon fiber implant may be employed in the reinforcing member 16.

Reinforcing member 16 can be osteogenic, osteoconductive, and/or osteoinductive. Osteoconductive materials that may be used include but are not limited to collagen and the various forms of calcium phosphates including hydroxyapatite, tricalcium phosphate, and fluoroapatite. Suitable osteoinductive substances include but are not limited to bone morphogenetic proteins (e.g., rhBMP-2), demineralized bone matrix, transforming growth factors (e.g., TGF-beta), osteoblast cells, and various other organic species known to induce bone formation. Bone marrow, blood plasma, or morselized bone of the patient, or commercially available materials may also be used.

The reinforcing member 16 may be treated prior to implantation. For example, the reinforcing member 16 may be dipped or coated with bone conductive or bone inductive material. Osteoinductive materials, such as BMP, may be applied to, for example, by immersing the reinforcing member 16 in an aqueous solution of this material in a dilute suspension of type I collagen. Osteoinductive materials such as TGF-beta may be applied from a saline solution containing an effective concentration of TGF-beta, or may be carried in the resilient material. Of course, other biologics may be applied by any method known in the art.

The reinforcing member can be resorbable or non-resorbable. For example, the reinforcing member 16 may comprise PEEK, PGA, or PLA material. Electrical stimulation can also be applied to the bone to promote bone healing. The reinforcing member 16 may also be capable of imbibing bone stimulating material, such as porous nitinol, e.g., ACTIPORE™ or other form of porous coated titanium or periapatite coated titanium.

In some embodiments, implantation of the reinforcing member 16 may be achieved step-wise in multiple stages. For example, the reinforcing member 16 may be constructed to be implanted at an initial stage to establish primary fixation, then at a subsequent stage additional implantation or assembly can be performed to add increased pull-out strength and other reinforcing properties to the fully assembled reinforcing member 16.

Other forms of implantable devices and variations of the reinforcing member 16 are also disclosed in co-pending and co-owned U.S. patent application Ser. No. 12/950,306, filed Nov. 19, 2010 and entitled "IMPLANTABLE DEVICES FOR SUBCHONDRAL TREATMENT OF JOINT PAIN," U.S. patent application Ser. No. 12/950,273, filed Nov. 19, 2010 and entitled "IMPLANTABLE DEVICES FOR SUBCHONDRAL TREATMENT OF JOINT PAIN," and U.S. patent application Ser. No. 12/950,183, filed Nov. 19, 2010 and entitled "BONE-DERIVED IMPLANTABLE DEVICES FOR SUBCHONDRAL TREATMENT OF JOINT PAIN," the contents of which are herein incorporated in their entirety by reference.

Figure 2A:
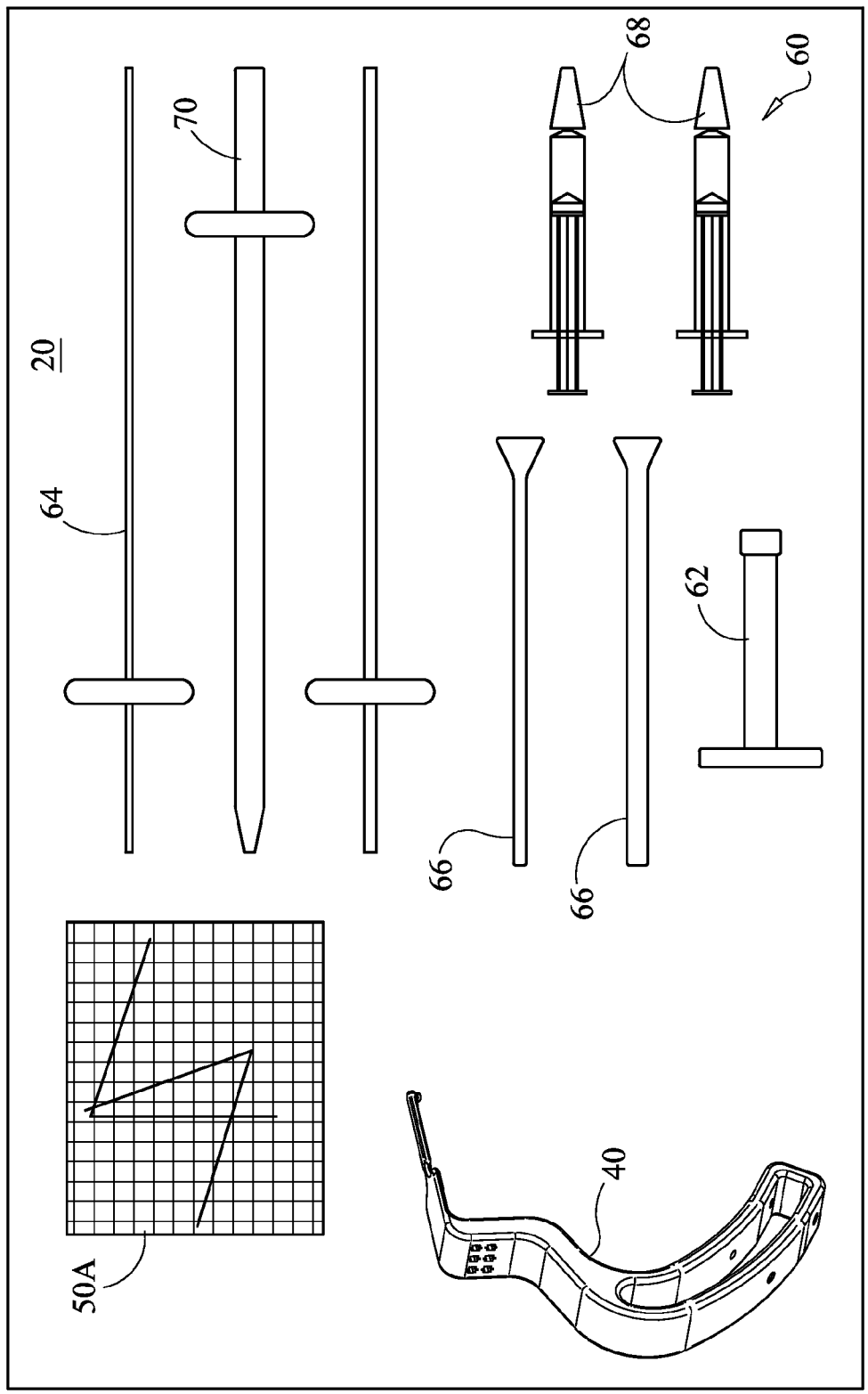
FIGS. 2A and 2B show exemplary SUBCHONDROPLASTY™ kits.
Figure 2B:
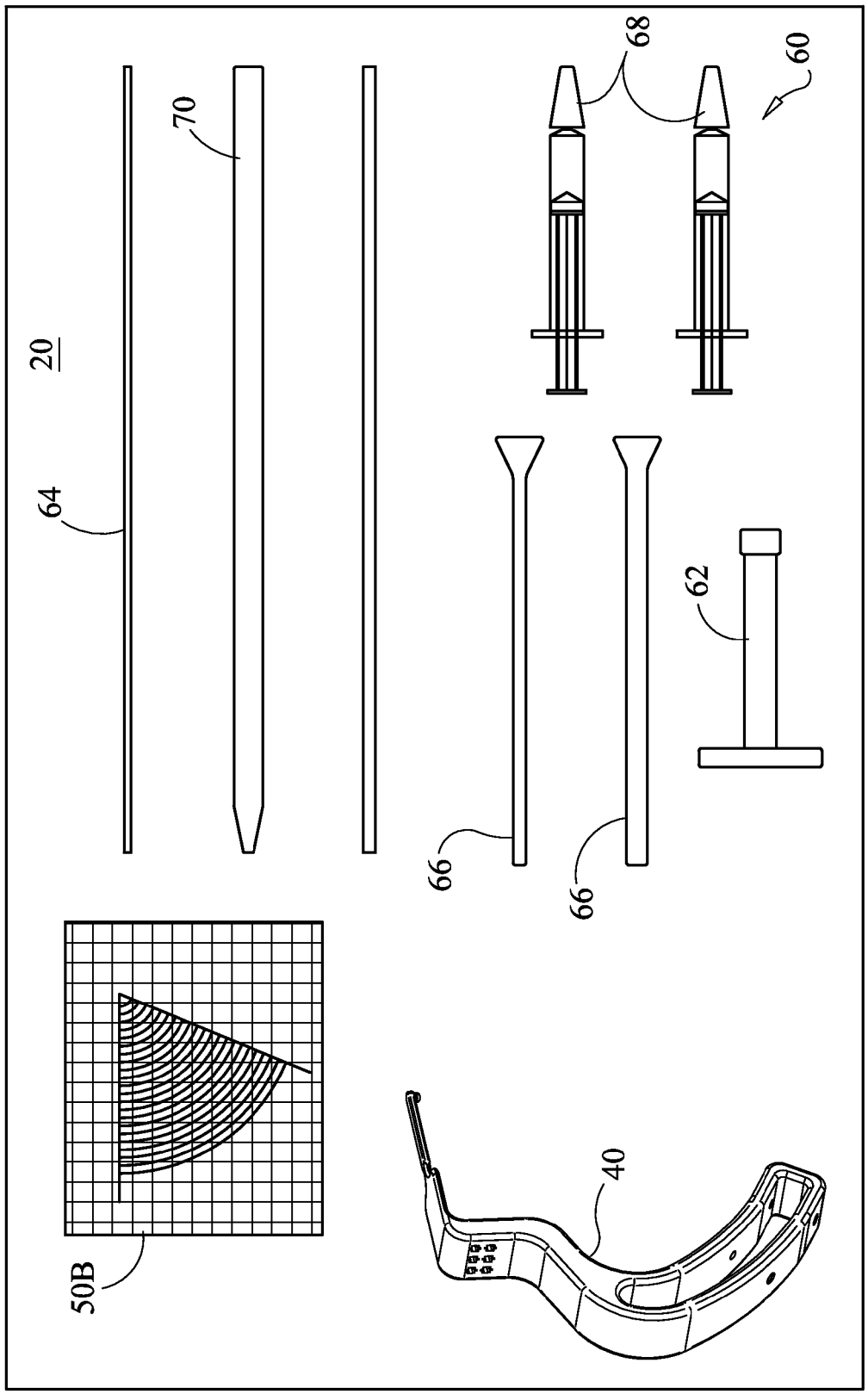

FIGS. 2A and 2B show exemplary SUBCHONDROPLASTY™ kits 20. These kits 20 are provided for facilitating the injection of bone void filler into subchondral insufficiency fractures in a subchondral surgical procedure that will be referred to under its marketed name as SUBCHONDROPLASTY™ or SCP™. As shown, the components of the kit may include, among other things, a SUBCHONDROPLASTY™ guide/insertion instrument 40, SCP™ templates 50A, 50B, and various tools 60 for assessment and/or drilling. For example, the tools 60 provided in kit 20 may include a volume assessment tool, a fixed bone portal 62, a Kirschner wire (or K-wire) 64, a bore creation device, several injection catheters 66 sized to match the bore creation device, several syringes 68, and a portal hole plug. In some embodiments, the kits 20 are provided to surgeon or medical facility pre-packaged and sterile. In addition, some or all of the instruments and tools provided in the kit 20 may be reusable or disposable.

The kits 20 may also include a cavity creation device (not shown in FIGS. 2A and 2B). Cavity creation devices may include burrs, punches, reamers, rongeurs, tamps, drills 70, instruments with expandable components, such as balloons, stents or looped wires, instruments with a selectively angulatable or reconfigurable distal ends, and others known in the art.

As shown, in FIG. 2A, a first embodiment of the kit 20 can include an assortment of reinforcing members, such as reinforcing member 16, of various sizes and/or shapes appropriate for use with a variety of bone lesions. The kit 20 can also include instructions for use, e.g., printed on the container and/or on inserts within the container. The kit 20 can still further include a tool for adjusting the size of the reinforcing member 16, a hammer for driving the reinforcing member 16 into the bone and/or a bone filler to seal the open end of the channel in the bone in which the reinforcing member 16 resides. As noted, the kit 20 may be prepackaged and sterile with an assortment of reusable or disposable instruments and tools.

Suitable bone fillers include but are not limited to materials comprising beta-tricalcium phosphate (e.g., VITOSS, PROOSTEON 500R made by E-Interpore-Cross International), hydroxyapatite (e.g., OSTEOGRAF made by Ceramed Denta, Inc., Lakewood, Colo.), calcium carbonate, calcium sulfate (e.g., OSTEOSET and ALLOMATRIX made by Wright Medical Technology, Inc.), calcium phosphate (e.g., CALCIBON made by Merck & Co., Inc., Whitehouse Station, N.J. and NORIAN SRS made by Synthes-Strates, Switzerland), synthetic bone fillers (e.g., CORTOSS) and/or processed bone fillers (e.g., BIOOSS made by Geistlich Biomaterials, Inc., Switzerland). Other suitable materials may include hydrogels, PEEK (polyetheretherketone), carbon fiber, polycarbonate urethane (PCU), stem cells with and without matrices, collagen with and without matrices and carriers, pharmacotherapeutic with and without matrices and carriers, hyaluronic acid with and without matrices, in situ curable materials with and without anti-inflammatory agents, demineralized bone matrix, allograft, biocompatible metals, resorbable PCA, PGLA, and polyurethane, hydroxyapatite, calcium sulfate, BMP growth factor, TGF-β super family, MP52, TP508, bioactive glass, sodium alignate, AOC based carrier and active components (synthetic beeswax), and starch.

In some embodiments, the bone filler may be of a type that can expand upon insertion into the void. For example, the filler may be injectable at the defect site, whereupon it can fill up or expand into the void. And as with the reinforcing member 16, the bone void filler may also be implanted in a step-wise fashion such that an initial stage to establish primary fixation is followed with a subsequent stage of assembly that provides added strength and bone integration properties to the fully assembled bone void filler.

As shown in FIG. 2B, another embodiment of the kit 20 can include a fluid, a syringe for injecting the fluid into a bone and a container adapted to maintain the sterility of the contents of the container. As noted, the kit 20 may be prepackaged and sterile with an assortment of reusable or disposable instruments. This embodiment of the kit 20 can further comprise a needle and premeasured portions of ingredients in a plurality of separate vials. As with the first embodiment of the kit 20, this embodiment can optionally include instructions for use, e.g., printed on the container and/or on inserts within the container. The kit 20 can further include bone tools for providing a channel in the bone in which the fluid is injected and/or a bone filler to seal the open end of the channel in the bone in which the reinforcing member resides.

The kit 20 can further include curing agents (i.e., polymerizing agents, catalysts and/or cross linking agents) as separate ingredients to be added to the injected fluid. The kit 20 can include other curing means, such as a UV light source or other device for generating radiation. The fluid can be preloaded in the syringe for injection. In some embodiments, a multiple barrel syringe can be included for in situ mixing of ingredients that must be stored separately in different barrels of the syringe (e.g., monomers and polymerizing agent, or polymers and cross linking agent, etc.).

Figure 3A:
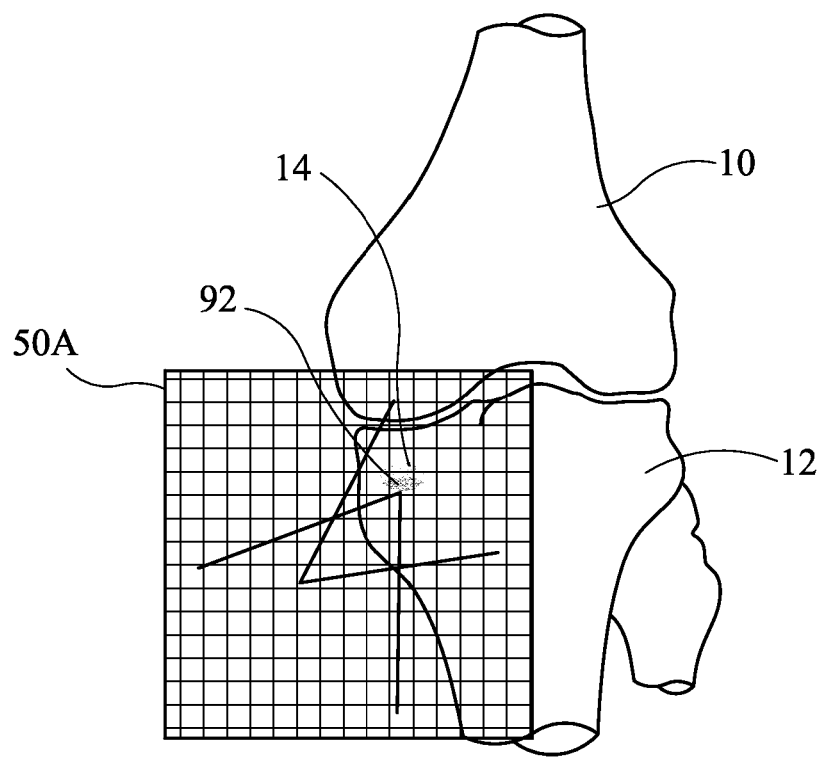
FIG. 3A shows a SUBCHONDROPLASTY™ template of the kit from FIG. 2A in use.
Figure 3B:
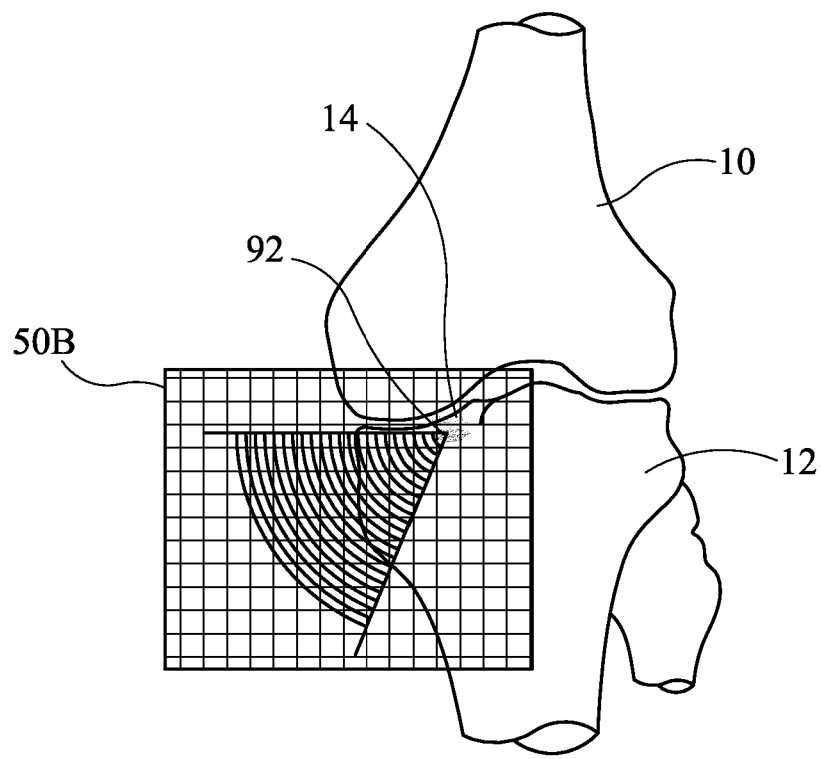
FIG. 3B shows a SUBCHONDROPLASTY™ template of the kit from FIG. 2B in use.

FIG. 3A shows a SUBCHONDROPLASTY™ template 50A of the kit 20 from FIG. 2A in use. FIG. 3B shows a SUBCHONDROPLASTY™ template 50B of the kit 20 from FIG. 2B in use. As part of the pre-operative planning process, medical imaging, such as an MRI illustrated in FIG. 1, is taken of the knee of a patient suffering from arthritic pain. For purposes of clarity, FIGS. 3A and 3B show the templates 50A, 50B overlaying a simplified illustration of a knee. A subchondral insufficiency fracture 92 associated with lesion 14 may then be identified and located on the MRI. The fracture size, volume and orientation are determined from the image, and based on the values, the recommended volume of bone void filler is determined from the volume assessment tool.

The SCP™ templates 50A and 50B, shown in FIGS. 3A and 3B, may be a transparent to indicate how a lesion can be treated. In use, for example, the templates 50A and 50B are placed over the MRI image to determine the placement of the SCP™ guide/insertion instrument 40, the appropriate location for a bone portal 62, and the resulting depth to the fracture.

Figure 4A:
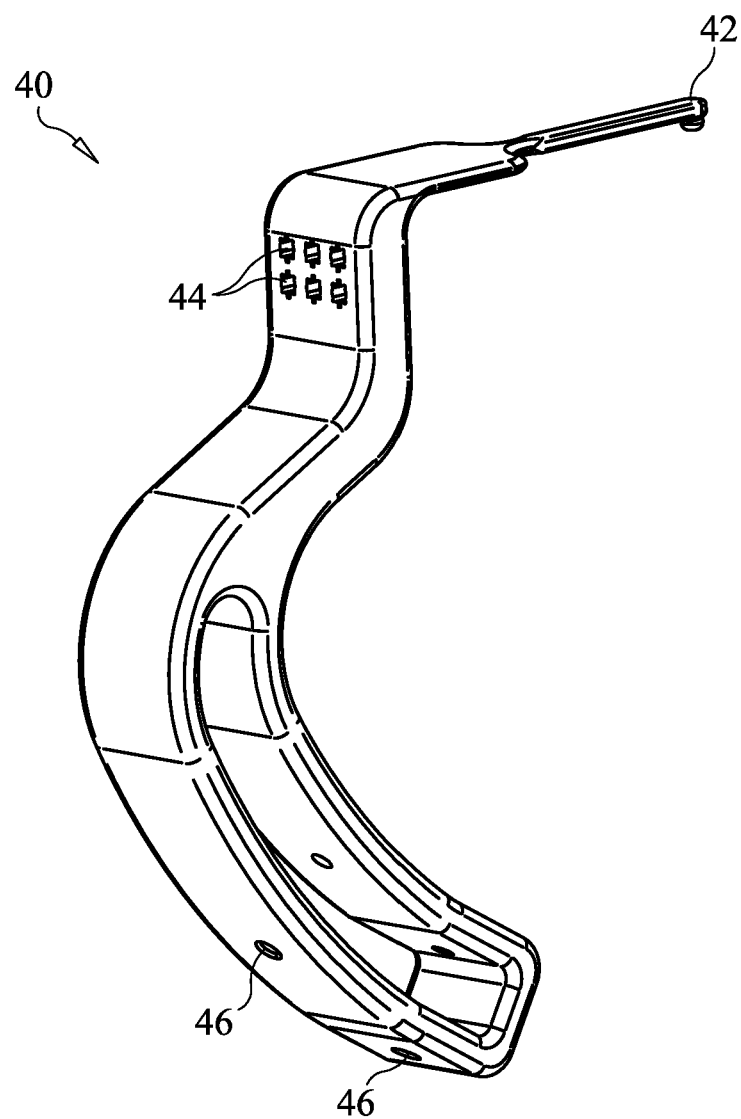
FIG. 4A shows an exemplary embodiment of the SUBCHONDROPLASTY™ guide/insertion tool or instrument.

FIG. 4A shows an exemplary embodiment of a SUBCHONDROPLASTY™ guide/insertion instrument 40. As shown, the guide/insertion instrument 40 may comprise an integrated cartilage reference 42, a parallel drill/implant guide 44, and angular drill guide/portal 46

The SCP™ guide/insertion instrument 40 is included in the kit 20 to aim the bone portal 62 and to set the depth stop of drilling for the surgeon. As shown, the SCP™ guide/insertion instrument 40 may comprise a curved body, a probe, and an optional adjustable arm (not shown). The curved body has a radius of curvature that provides for different angles of approach to the tip of the probe. The probe is attached to the curved body and may have a planar, rasped tip for contacting and gripping the articular surface of the knee joint without damaging the cartilage. The optional adjustable arm (not shown) may be connected to the curved body through a sliding arrangement such that the angle of the arm is adjustable with respect to the curved body.

Figure 4B:
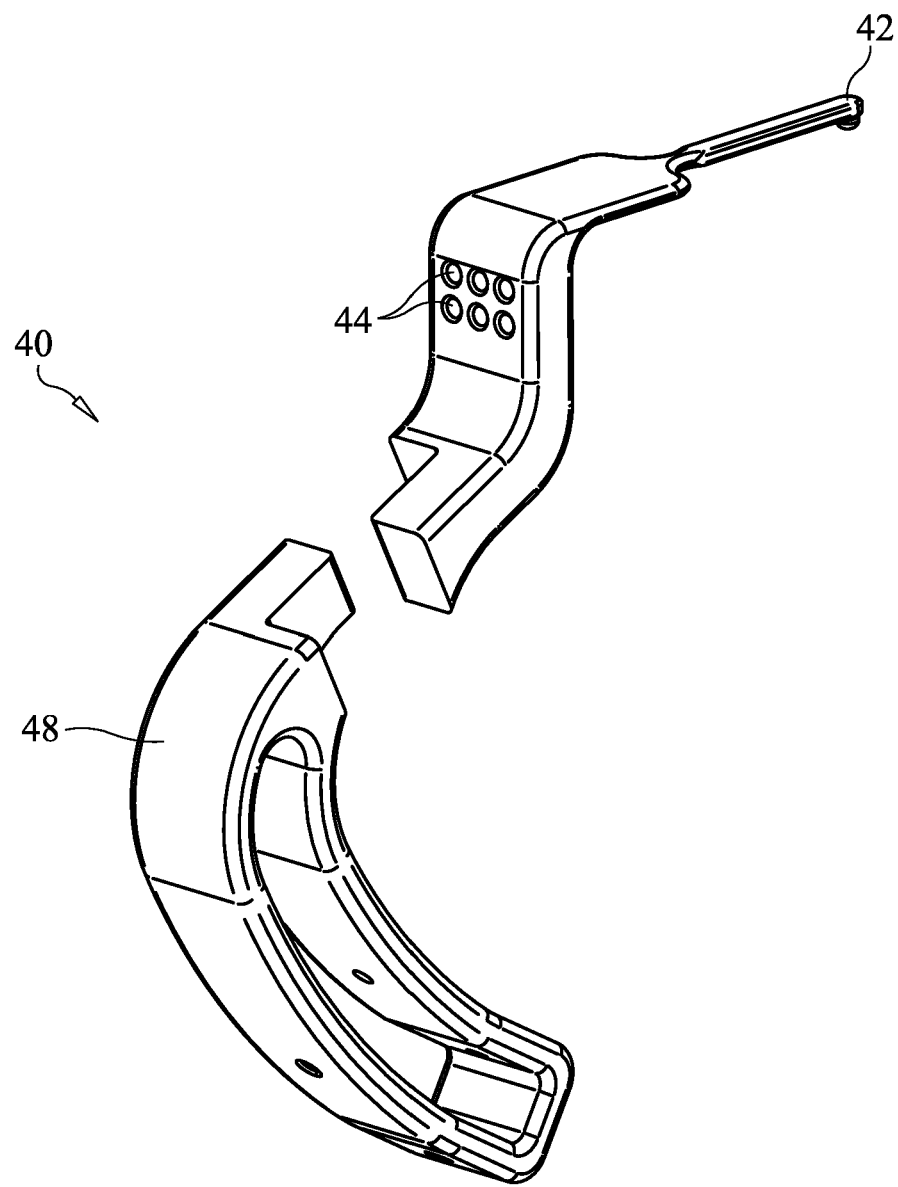
FIG. 4B shows another exemplary embodiment of the SUBCHONDROPLASTY™ guide/insertion tool or instrument.

FIG. 4B shows another exemplary embodiment of the SUBCHONDROPLASTY™ guide/insertion instrument 40. As shown, in this embodiment, the SCP™ guide/insertion instrument 40 may comprise a detachable handle 48. The detachable handle 48 may be detachable in order to facilitate its manipulation during surgery. The detachable handle 48 may be detachable based on various mechanisms that are known to those skilled in the art.

Figure 5:
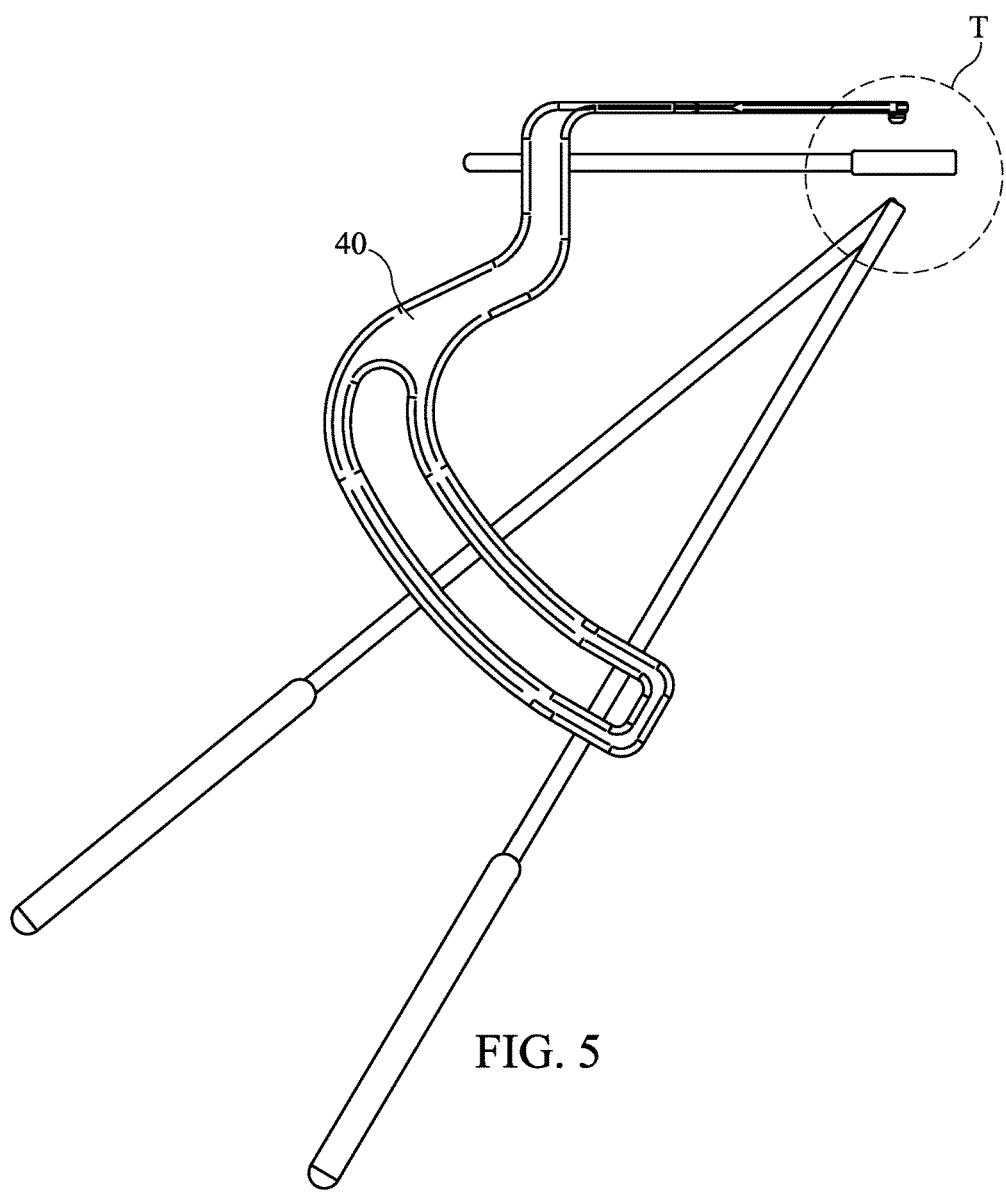
FIG. 5 illustrates a side view of a SUBCHONDROPLASTY™ guide/insertion instrument and various options of the guide/insertion instrument in use with other instruments of the kit.

FIG. 5 illustrates a side view of the SCP™ guide/insertion instrument 40 and various options of the instrument 40. As shown, the probe of the SCP™ guide/insertion instrument 40 may comprise integrated cartilage reference 42 and parallel drill/implant guide 44. The guide 44 is configured to guide a drill 70 or other tool to a location or target T indicated by the cartilage reference 42. In addition, in the embodiment shown, the curved body of the SCP™ guide/insertion instrument comprises an angular drill guide/portal 46. The guide/portal 46 may provide a set of guides/portals that converge at location T from various angles, such as 30 degrees and 45 degrees.

Figure 6:
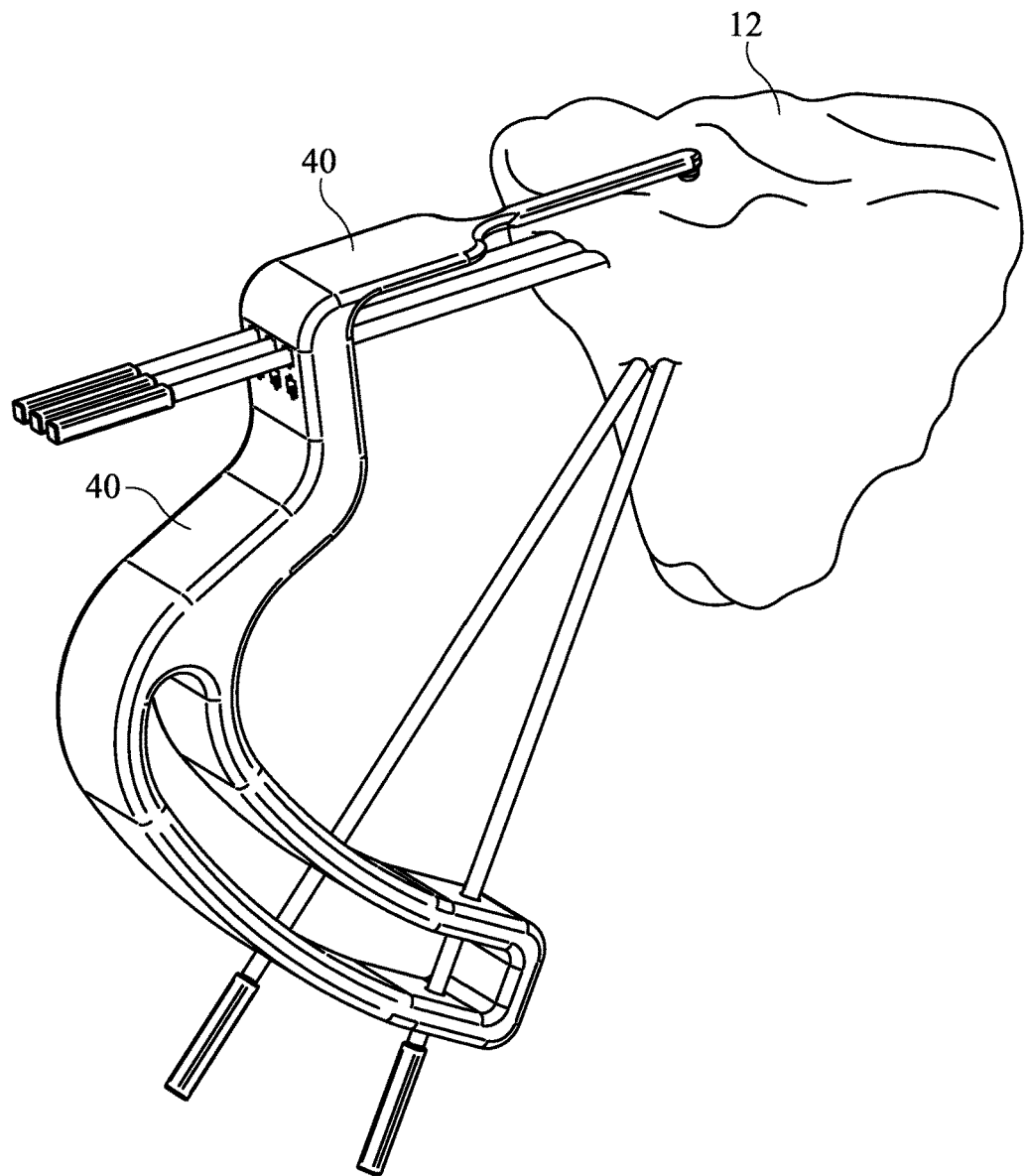
FIG. 6 illustrates a perspective view of the various options of the SUBCHONDROPLASTY™ guide/insertion instrument in use with other instruments of the kit.

FIG. 6 illustrates a perspective view of the various options of the SUBCHONDROPLASTY™ guide/insertion instrument 40. As shown, the parallel drill/implant guide 44 may comprise a series of holes/portals in a matrix configuration to help guide a drill 70 or other tool to location T.

Figure 7A:
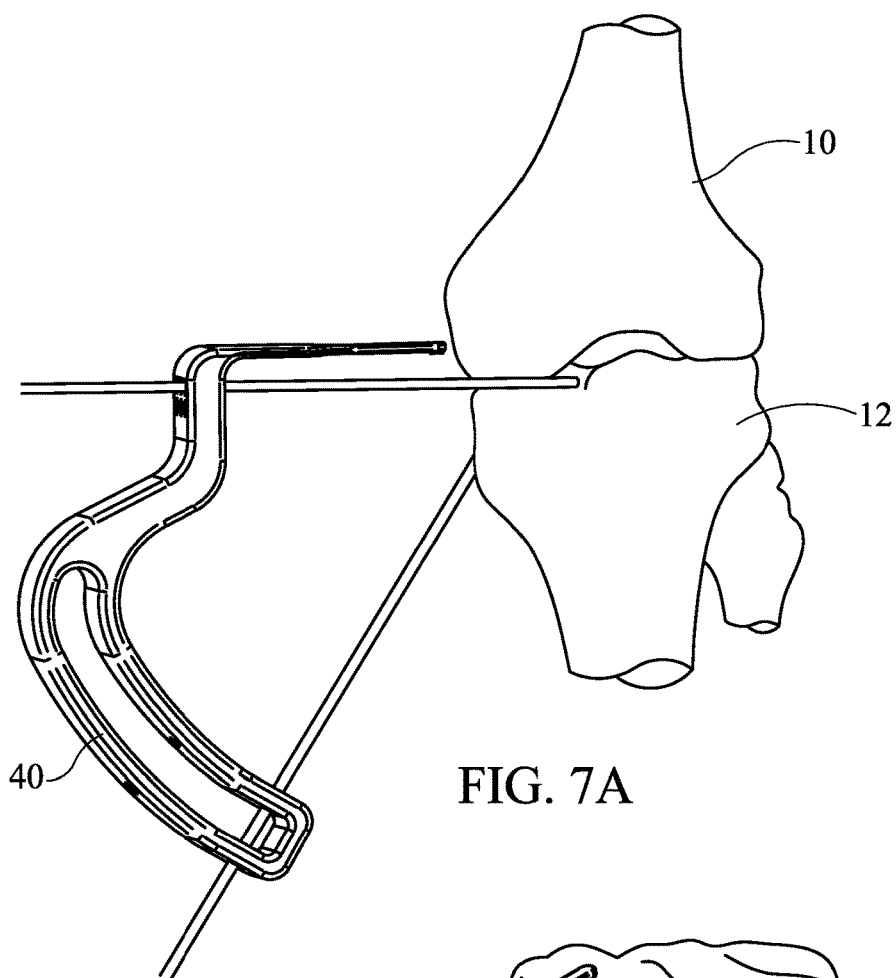
FIG. 7A shows one embodiment of a SUBCHONDROPLASTY™ guide/insertion instrument and a side view of how the guide/insertion instrument may be placed relative to a knee.
Figure 7B:
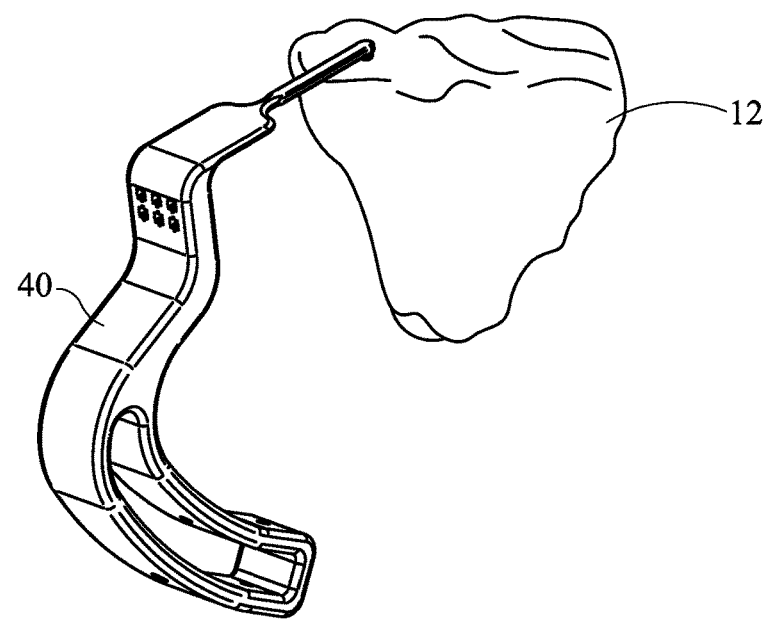
FIG. 7B shows another embodiment of a SUBCHONDROPLASTY™ guide/insertion instrument and a perspective view of how it may be placed relative to a knee.

FIG. 7A shows another embodiment of a SUBCHONDROPLASTY™ guide/insertion instrument 40 and side view of how it may be placed relative to a knee during surgery. FIG. 7B shows the SUBCHONDROPLASTY™ guide/insertion instrument 40 and a perspective view of how it may be placed relative to a knee.

FIGS. 8, 9A-9J, 10A-10B, 11A-11C illustrate a method of treating a knee based on embodiments of the present invention. As noted, medical imaging, such as an MRI, is taken of the knee of a patient suffering from arthritic pain. A bone marrow lesion, such as a subchondral insufficiency fracture 92, is identified and located on the MRI. The fracture size, volume and orientation are determined from the image, and based on the findings, the recommended volume of bone void filler is determined from the volume assessment tool. The SCP™ template, shown in FIGS. 3A and 3B, is a transparency with a plurality of curved lines between two intersecting straight lines. In use, the template 50 is placed over the MRI image to determine the placement of the SCP™ guide/insertion instrument 40, the appropriate location for the fixed bone portal 62, and the resulting depth to the fracture.

Figure 8:
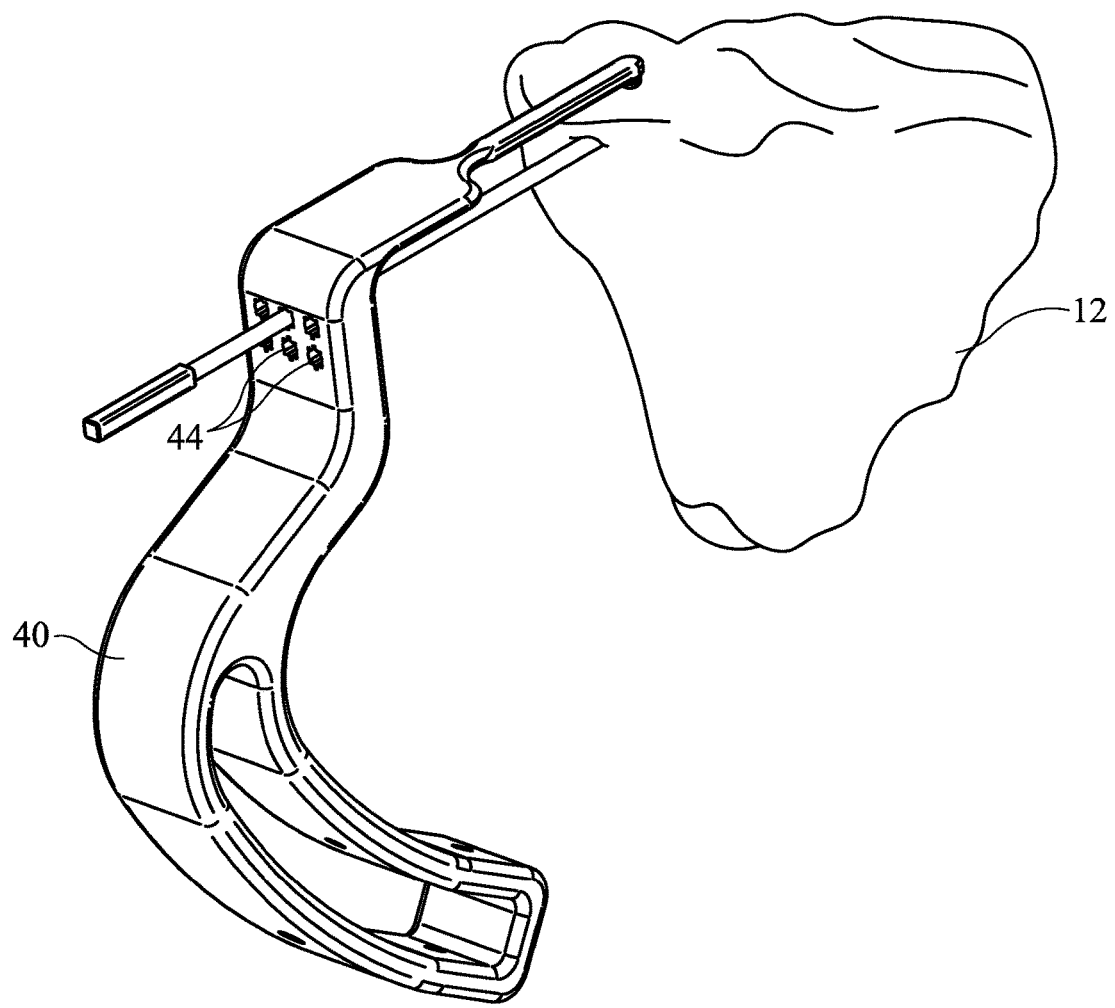
FIGS. 8, 9A-9J, 10A-10B, and 11A-11C illustrate a method of treating a knee based on embodiments of the present invention.

Referring now to FIG. 8, the SCP™ guide/insertion instrument 40 may be positioned such that the location T of the cartilage guide 42 is in on or adjacent to the bone marrow lesion of interest. In use, the SCP™ guide/insertion instrument 40 is placed proximate to the joint. The probe may be visually placed on the articular cartilage, for example, using arthroscopy. If present, any cartilage defect can be used to assist probe placement.

The SCP™ guide/insertion instrument 40 helps determine the access point and angle for the K-wire (included in the kit 20), which may be used by the surgeon. For example, in some embodiments for treating a patient's knee, the SCP™ guide/insertion instrument 40 is configured to treat subchondral bone that is within 5 mm below the tibial surface. In some embodiments, the SCP™ guide/insertion instrument 40 has a planar, rasped tip for contacting and gripping the articular surface of the knee joint without damaging the cartilage.

Using parallel drill/implant guide 44, a surgeon may then drill parallel, for example, to the articular surface of a patient's knee. In some embodiments, the surgeon drills through or adjacent to the bone marrow lesion.

Figure 9A:
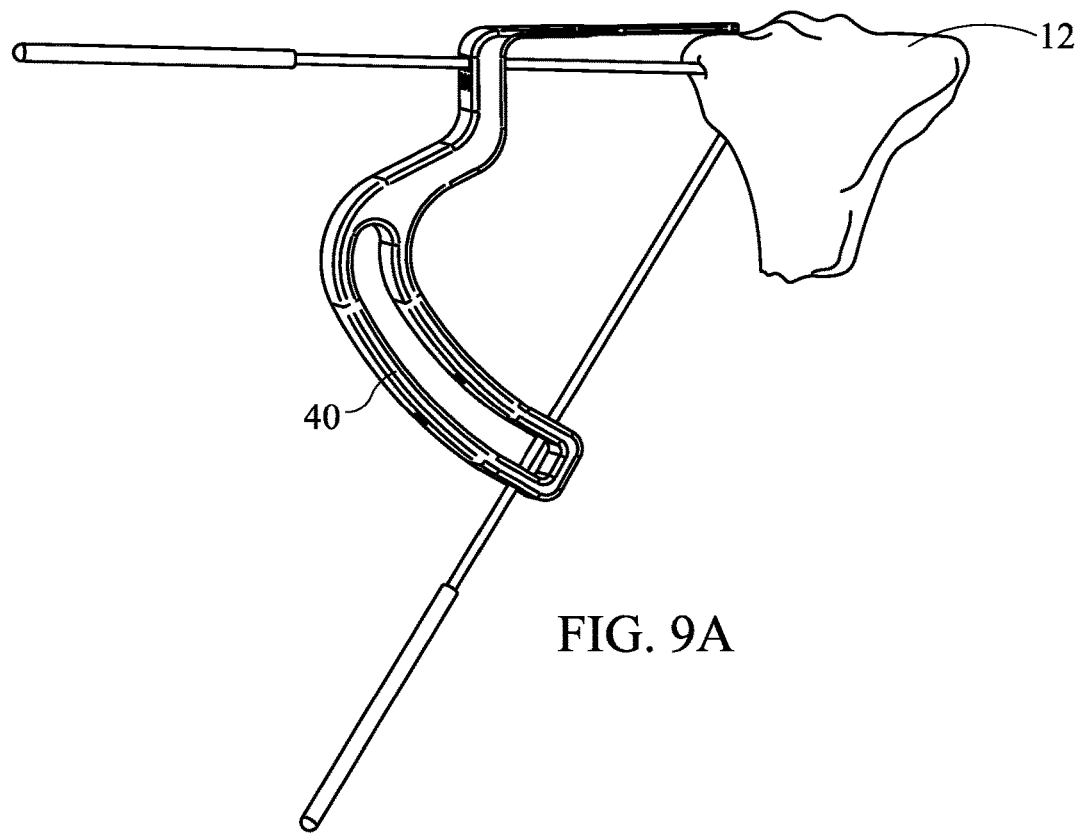

Referring now to FIG. 9A, the surgeon may then drill at an angle to location T of the bone marrow lesion 92 via angular drill guide/portal 46. The surgeon may select the angle of approach based on a variety of factors, such as the location of the bone marrow lesion, size of the lesion, access to the knee, etc. While the SCP™ guide/insertion instrument 40 is held in place, a K-wire is inserted through the lumen in the adjustable arm and into interior of the bone. Fluoroscopy may be used to verify the position and depth of the wire with respect to the fracture 92. The SCP™ guide/insertion instrument 40 may then be removed, but the K-wire retains the angle and depth to the fracture 92.

Figure 9B:
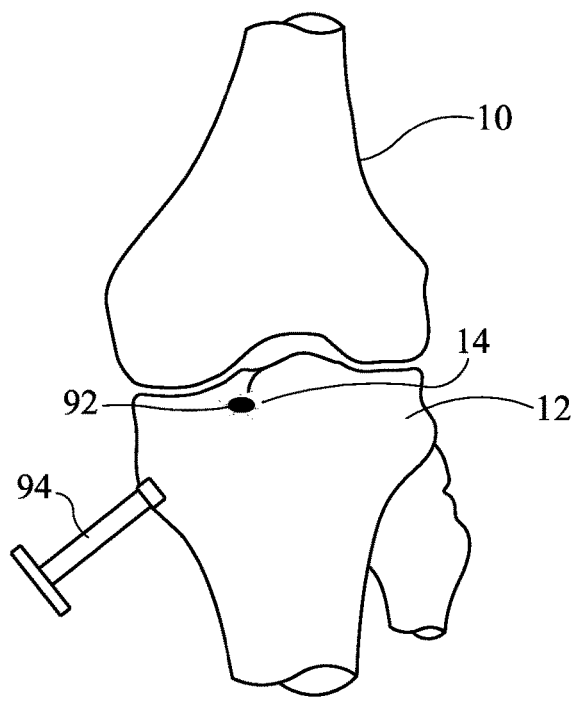
Figure 9C:
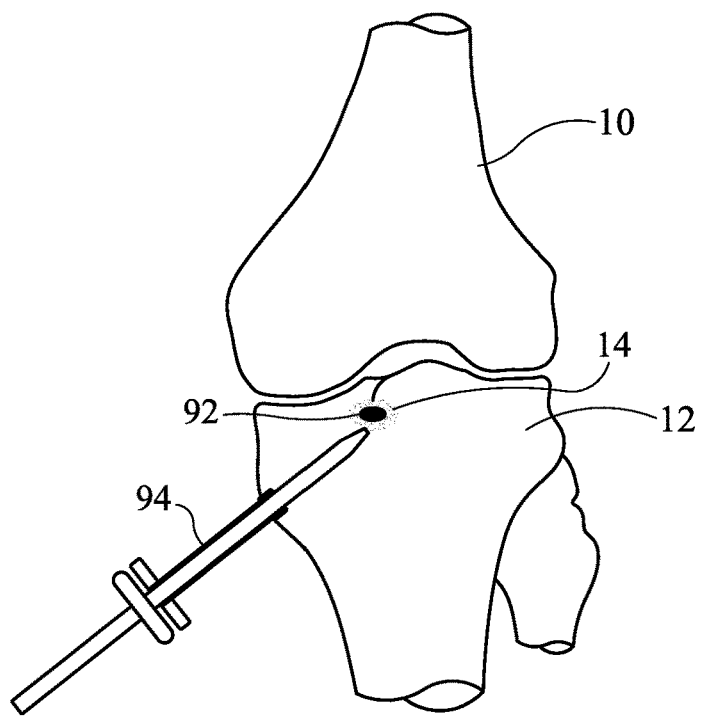
Figure 9D:
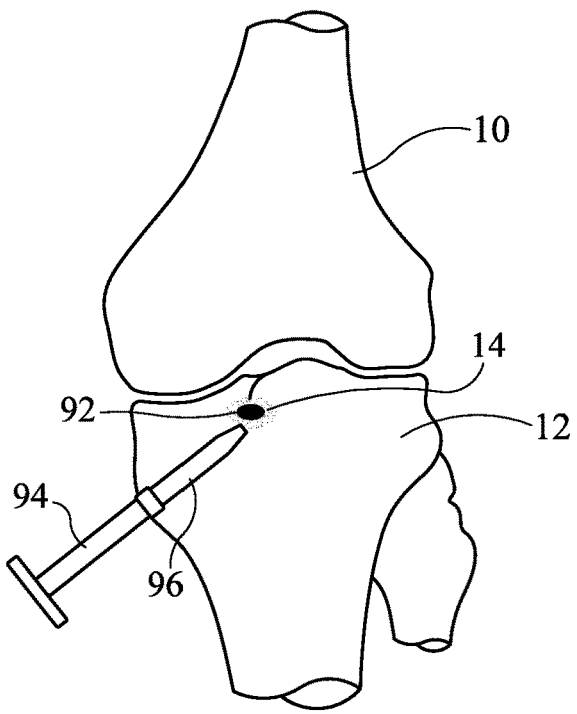

FIGS. 9B-9D illustrate in further detail how a surgeon may drill at an angle to a bone marrow lesion 92. As shown, the surgeon may install a bone portal 94, for example, using the SCP™ guide/insertion instrument 40 (not shown).

In use, the SCP™ guide/insertion instrument 40 is placed proximate to the joint. Based on the information determined from the SCP™ template, the probe tip of SCP™ guide/insertion instrument 40 is placed on a target location on the articular surface of the knee joint, i.e., in or adjacent to the bone marrow lesion. As noted above, in order to treat knee pain, the bone marrow lesion 14 may be a meniscal defect associated with an underlying subchondral insufficiency fracture 92.

The guide/insertion instrument 40 is used to aim a bone portal angle and to set the bone portal depth stop based on the information determined from the SCP™ template. The SCP™ guide/insertion instrument 40 may then be removed and the bone portal retains the angle to the fracture location. During surgery, the bone portal may also hold or steady the SCP™ guide/insertion instrument 40.

The bone portal 62 (included in the kit 20) provides an entry point in the bone for an instrument to gain access to the interior of the bone and to the subchondral insufficiency fracture 92. The bone portal 62 may be a single component design having an elongate body. The distal end of the body may include external threads for anchoring the portal 62 to the cortex of the bone. In some embodiments, the portal 62 has an outer diameter of approximately 8 mm. The size of a particular bone portal 62 is selected to support the cortex and prevent possible damage and weakening of the surrounding cortex. The body of the bone portal 62 has a lumen for receiving an instrument therein and a length that allows for an accurate trajectory to the bone marrow lesion 14. The proximal end of the body has a depth stop for limiting the extent an instrument received within the lumen may be inserted into the interior of the bone. To facilitate the ease of implementing the SUBCHONDROPLASTY™ treatment, the bone portal 62 may serve as a working channel, enabling a multitude of instruments to pass through the same access point.

In use, the bone portal 62 can be threadedly anchored to the bone cortex at a location determined from the MRI template. As shown, the bone portal 62 is installed at an angle perpendicular to the bone cortex, resulting in better coupling. Alternatively, the surgeon may use an adjustable bone portal 62 that allows for repeated entry into the bone for multiple fractures to be treated with a single bone portal insertion. The portal 62 may be made of a resorbable material, in which case it could provide as an implant left in the cortex after the SCP™ procedure is completed. Furthermore, the bone portal 62 may be radiolucent and have at least one marker for identification under imaging.

The surgeon may then drill through the SCP™ guide/insertion instrument 40 via angular drill guide/portal 46 (not shown) to create a bone cavity 96 to bone marrow lesion (as shown in FIG. 9D). The drill may be a cannulated drill 70, for example that is used over the K-wire to enlarge the channel to the fracture 92. Other bore creation devices known in the art may be used, including biopsy needles, punches, burrs, reamers, rongeurs and tamps, as well as other types of drills.

Figure 9E:
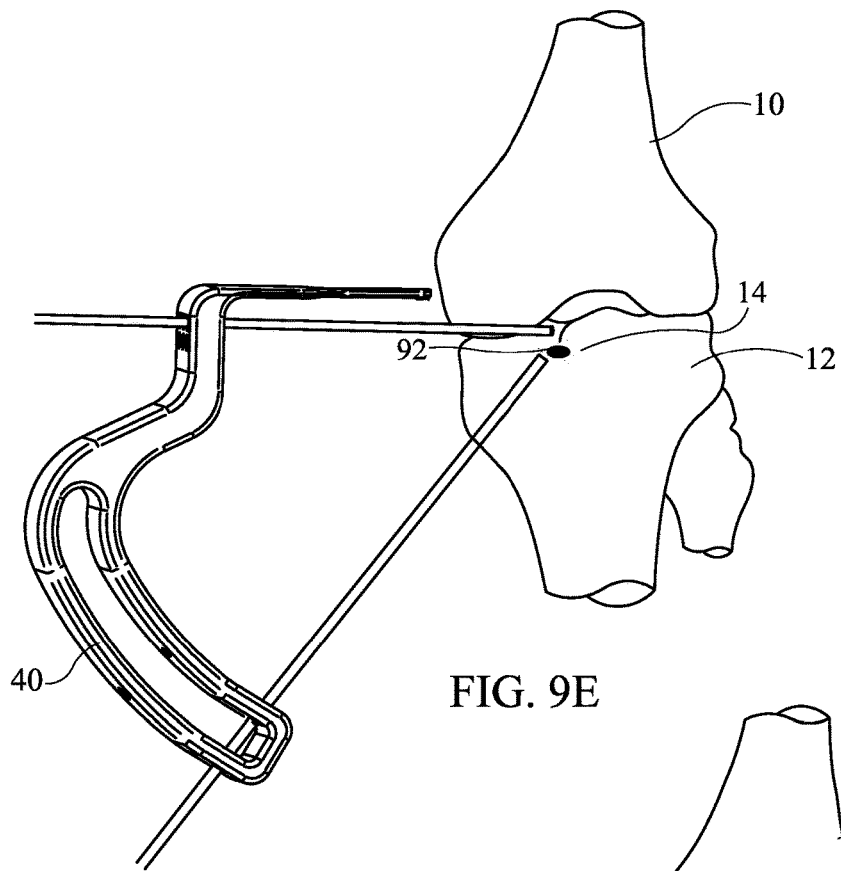

FIG. 9E illustrates how the surgeon may then employ a Kirschner wire or K-wire at the site of bone marrow lesion 92. Alternatively, FIG. 9F shows the use of an adjustable bone portal 98 that allows the surgeon to select one or more angles provided by angular drill guide/portal 46 or, for example, to treat multiple sites.

Figure 9F:
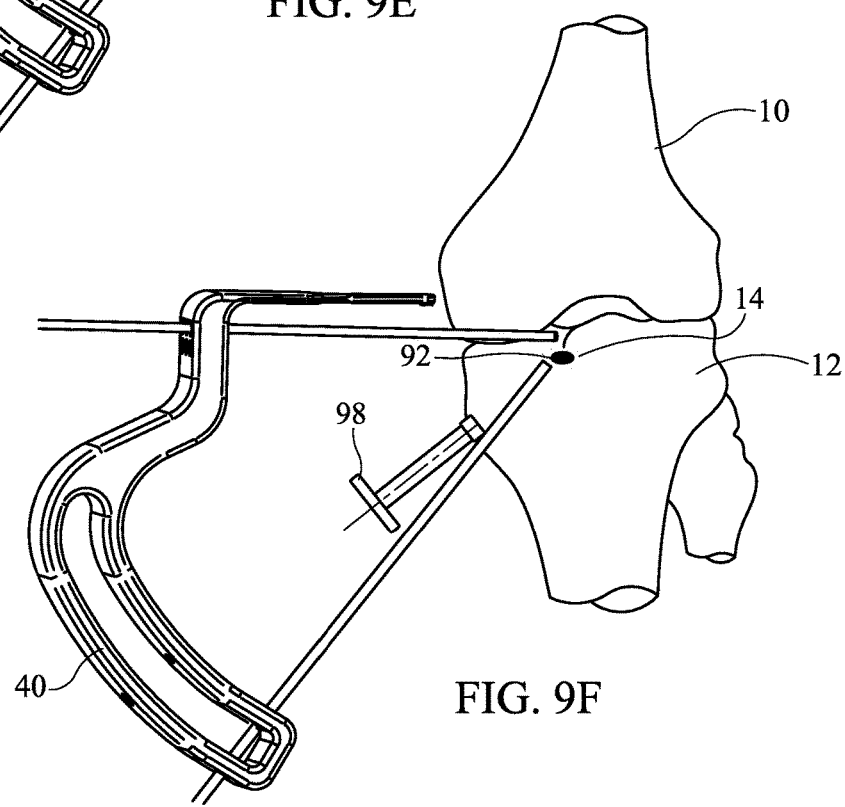
Figure 9G:
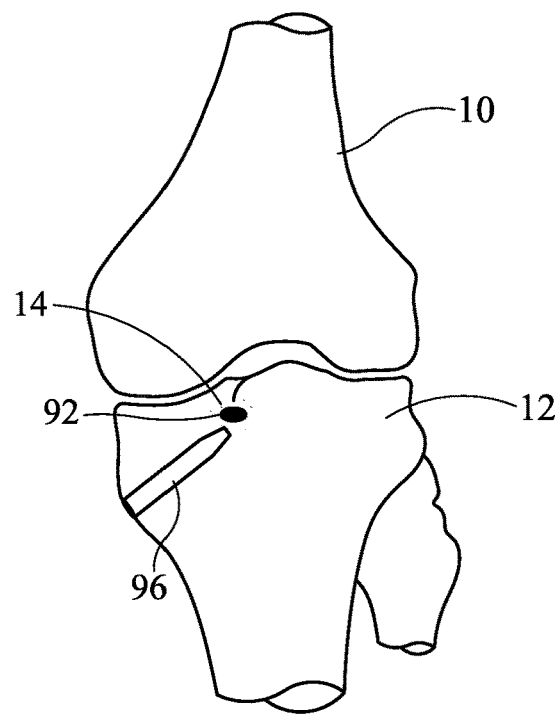
Figure 9H:
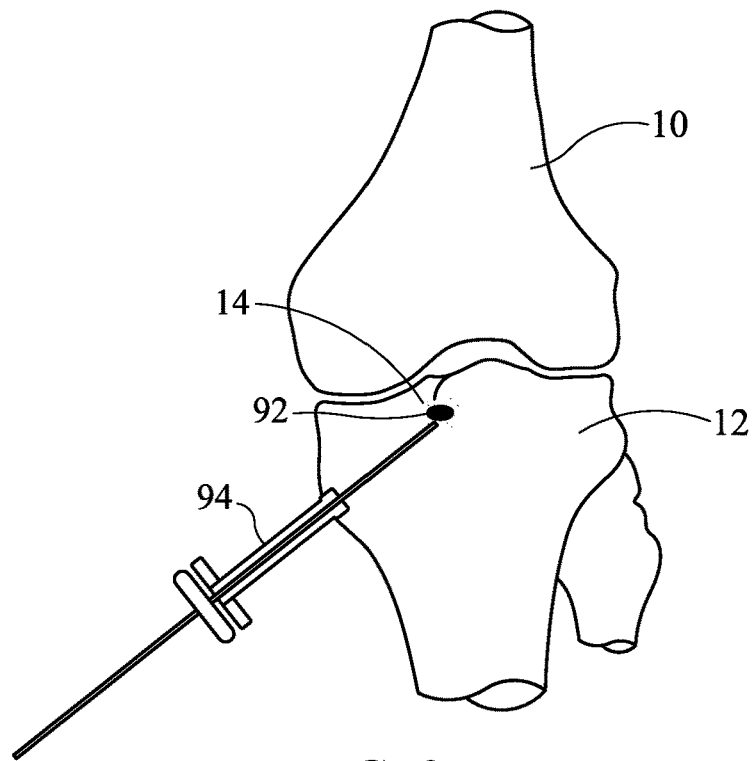
Figure 9I:
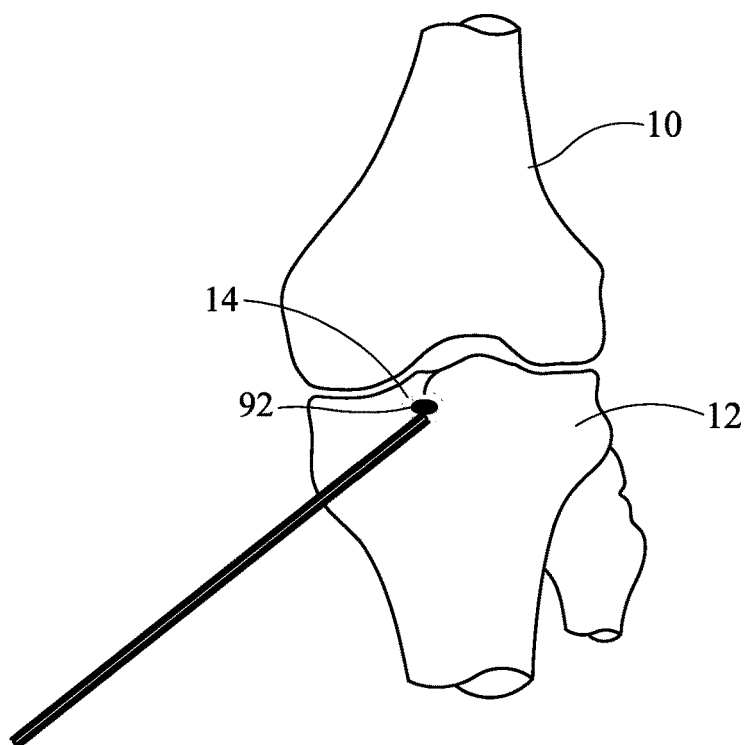
Figure 9J:
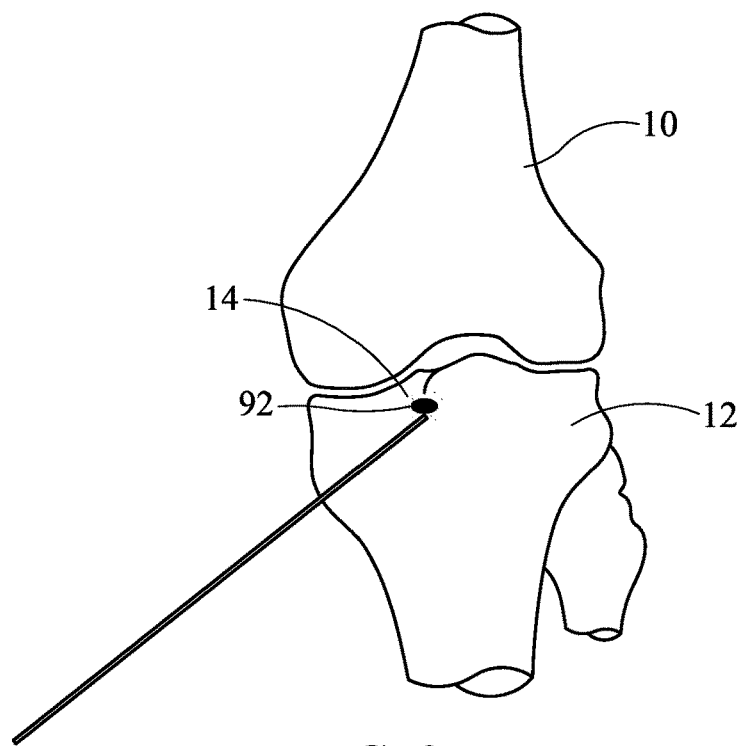

The adjustable bone portal shown in FIG. 9F may be included in the kit 20 to provide an entry point in the bone for different instruments to gain access to the interior of the bone and to a subchondral insufficiency fracture 92, as previously mentioned. In general, the adjustable bone portal has a body component and base component. The base component includes external threads for anchoring the portal to the cortex of the bone and a central opening for receiving the body component. The outer diameter of the base component is approximately 8 mm, selected to support the cortex and prevent possible damage and weakening of the surrounding cortex with a portal with a larger diameter. The body component may have a lumen for receiving different instruments, and a length that allows for an accurate trajectory to the defect. A proximal end of the body component has a depth stop for limiting the extent an instrument received within the lumen may be inserted into the interior of the bone. The depth stop may be adjusted according to the depth of the defect within the bone, as measured from the entry point.

In some embodiments, adjustability of the bone portal is achieved through a ball-and-socket arrangement between a socketed central opening in the base component and a ball shaped distal end of the body component. A lock mechanism can be provided to maintain the base and body components in a desired position relative to each other. In another embodiment, adjustability of the bone portal is achieved through a conically shaped central opening in the base component. A locking mechanism can be provided to maintain the base and body components in a desired position relative to each other.

FIGS. 9G-9J illustrates the various ways that a surgeon may treat a knee via bone cavity 96. A cavity creation device is used after a bore creating device is removed to leave an enlarged channel to the fracture, and prior to the bone void filler being prepared As shown, the surgeon may use a K-wire with a depth stop (included in the kit 20) to create an access channel to the subchondral insufficiency fracture 92. As shown in FIG. 9G-9J, the K-wire is inserted through the lumen of the bone portal body to the desired depth, which will be reached when the K-wire depth stop contacts the bone portal body depth stop. The K-wire is prevented from being advanced through the articular surface. Fluoroscopy may be used to verify the K-wire position and depth with respect to the fracture. If placement is incorrect, the K-wire can be retracted and the bone portal readjusted. The K-wire 64 is then removed.

The surgeon may use a bore creation device (also included in the kit 20) to enlarge the access channel created by the K-wire 64 to the fracture. The bore creation device can be an 8-gauge biopsy needle, a core punch, or a fenestrated drill. Each can be provided with a depth stop to prevent penetration through the articular surface of the bone. Other bore creation devices known in the art may be used, including burrs, reamers, rongeurs and tamps, as well as other types of biopsy needles, punches and drills. A cavity creation device in the form of a burr, for example, is inserted through the lumen in the bone portal to the desired depth and is manually moved or activated to create a cavity. Depending on the device used, this may be accomplished by cutting bone, compressing bone, or a combination. In addition, it has been discovered that the bone tissue surrounding a bone marrow lesion tends to be relative soft (usually, edema is present) compared with normal, healthy bone tissue. Accordingly, according to SCP™, the surgeon may also treat the lesion or defect by compacting the soft bone tissue.

As shown, the surgeon may use a cannulated drill, for example, being inserted through the lumen of the bone portal body until the drill depth stop contacts the bone portal body depth stop. The drill is prevented from being advanced through the articular surface. The drill is then removed, leaving an enlarged channel 96 to the fracture 92.

In another embodiment, a series of cannulas or bone dilators of progressively increasing diameter may be provided. The cannulas or dilators may be used to progressively bore concentric openings within the subchondral bone.

Figure 10A:
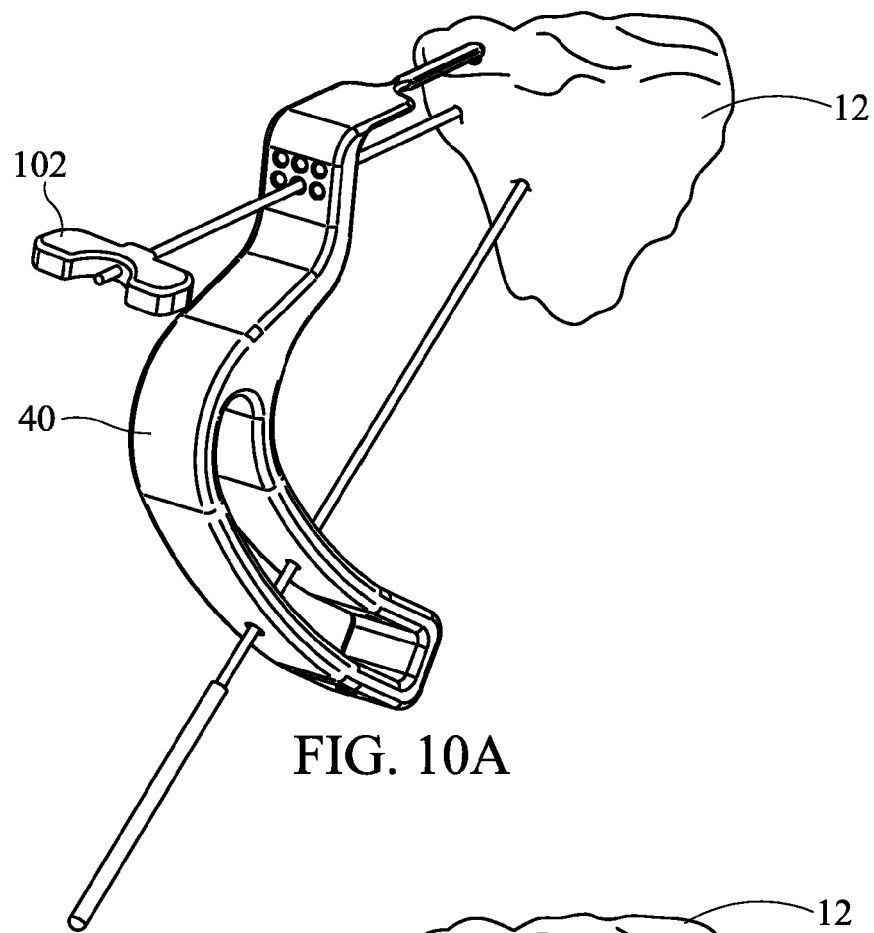

FIG. 10A illustrates another step that a surgeon may perform to treat a patient's knee. In particular, the surgeon may inject bone void filler, such as calcium phosphate (CaP) or a bone cement, such as a low viscosity Poly-methyl methacrylate ("PMMA"). During surgery, an injection catheter 66 is filled with a volume of the bone void filler, which was determined from the volume assessment tool (included in the kit 20). FIG. 10A shows the injection catheter 66 being inserted and sealed to the bone portal. Cement in the catheter 66 prevents bone shards and debris from clogging the catheter 66. Under fluoroscopy, the bone cement is injected from the catheter 66 into the subchondral insufficiency fracture 92 using a syringe 68 with volume and rate controls. The syringe 68 provides tactile feedback as the bone cement is dispensed to fill the fracture and then interdigitate with the immediately surrounding cancellous bone. The catheter 66, syringe 68 and bone portal 62 may then be removed.

In order to prevent bone void filler from leaking out of the hole that remains in the cortex after removal of the bone portal, a portal hole plug (provided in the kit 20) may be used. Alternatively, the bone that was removed using the bore creation device during the channel enlargement step may be sized and shaped as a plug to fill the portal hole. Of note, the injection of a bone void filler can be before or after the implantation of reinforcing member 16. If desired, the bone marrow lesion or edema may be aspirated prior to insertion of the implant or infusion of the bone void filler. This aspiration step may be performed through the angular drill guide/portal 46, and suction may be performed through the parallel drill/implant guide 44.

Figure 10B:
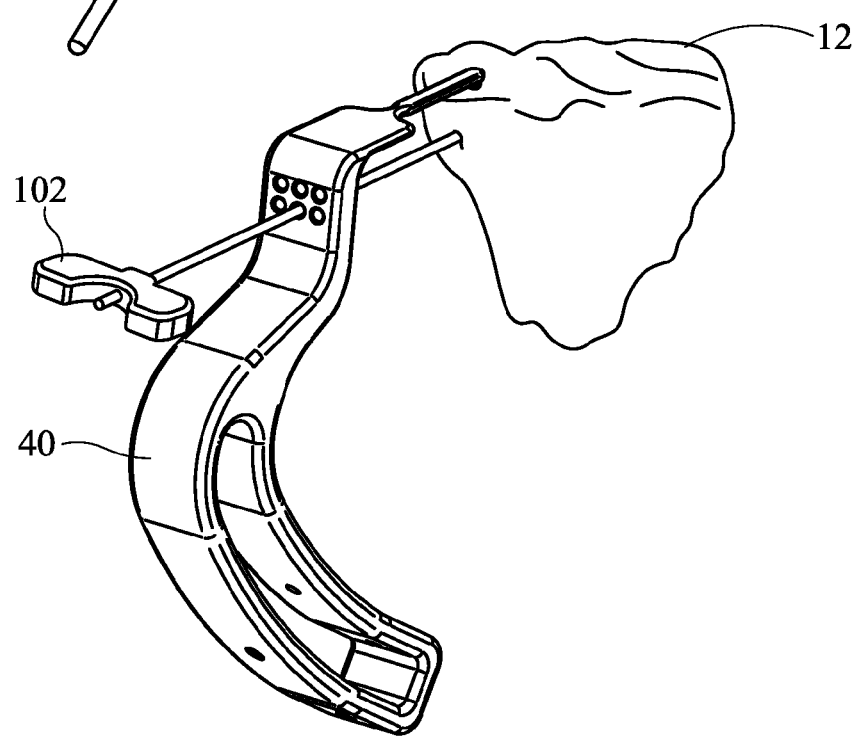

For example, as shown, an 8-gauge needle 102 may be guided via parallel drill/implant guide 44 in or adjacent to the bone marrow lesion. FIG. 10B illustrates another view of the surgeon injecting CaP cement via the parallel drill/implant guide 44. In some embodiments, the surgeon may drill one or more holes at various locations. In addition, the surgeon may leave the drill bits in place in order to stability the SCP™ tool guide 40.

Alternatively, the surgeon may insert one or more bone conductive pins through the SCP™ tool guide 40 and into pre-drilled holes. After the implants have been implanted, the SCP™ tool guide 40 may be removed and pins cut flush to the bone surface.

Figure 11A:
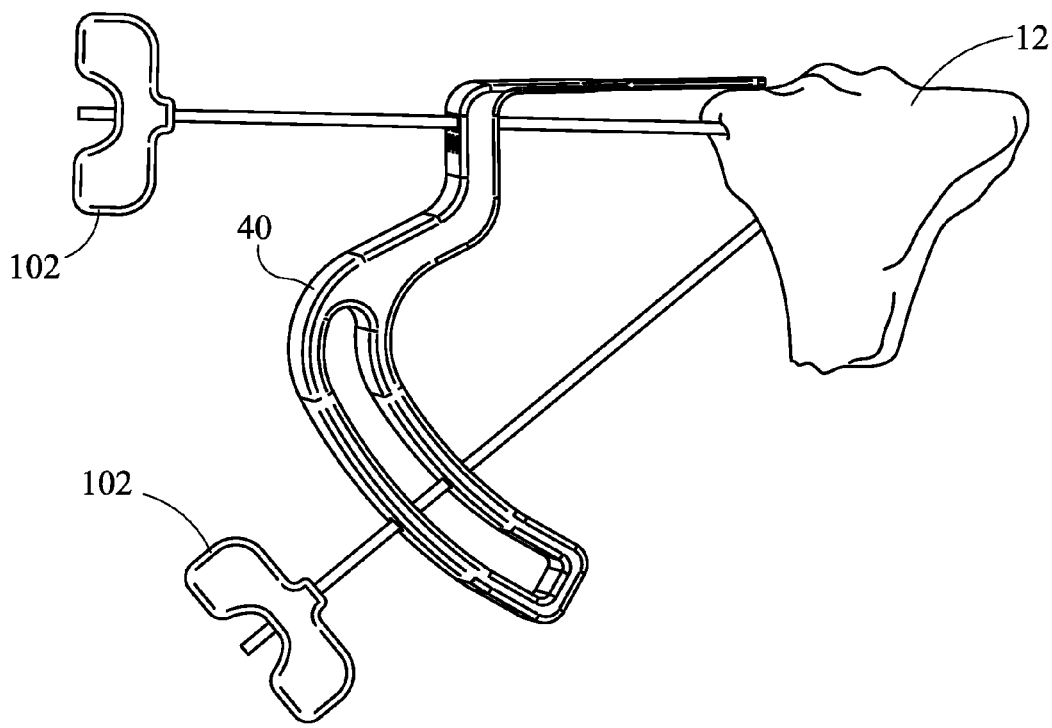
Figure 11B:
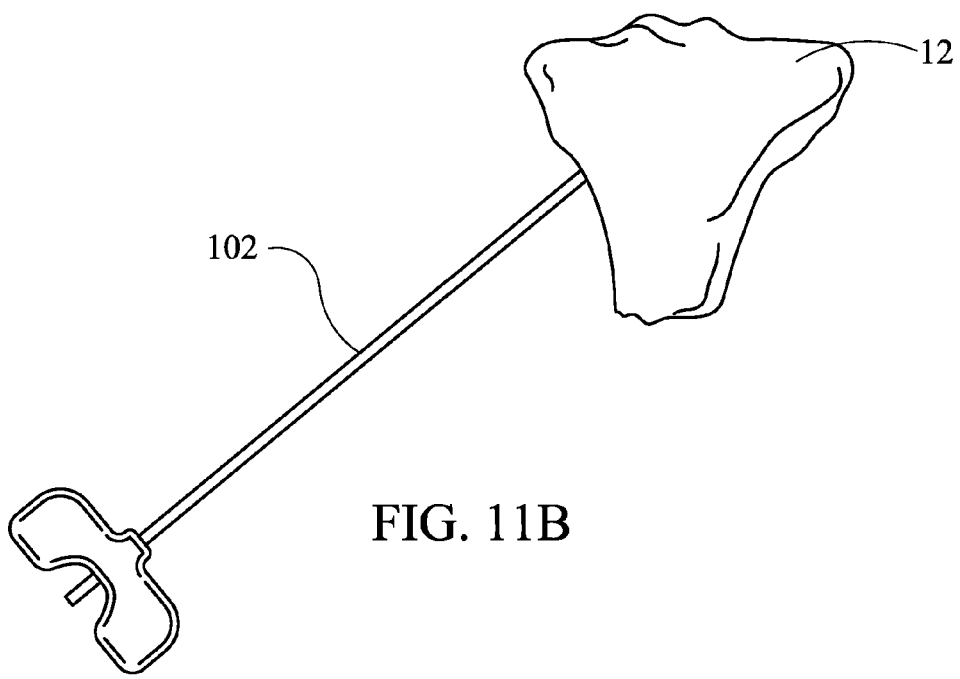
Figure 11C:
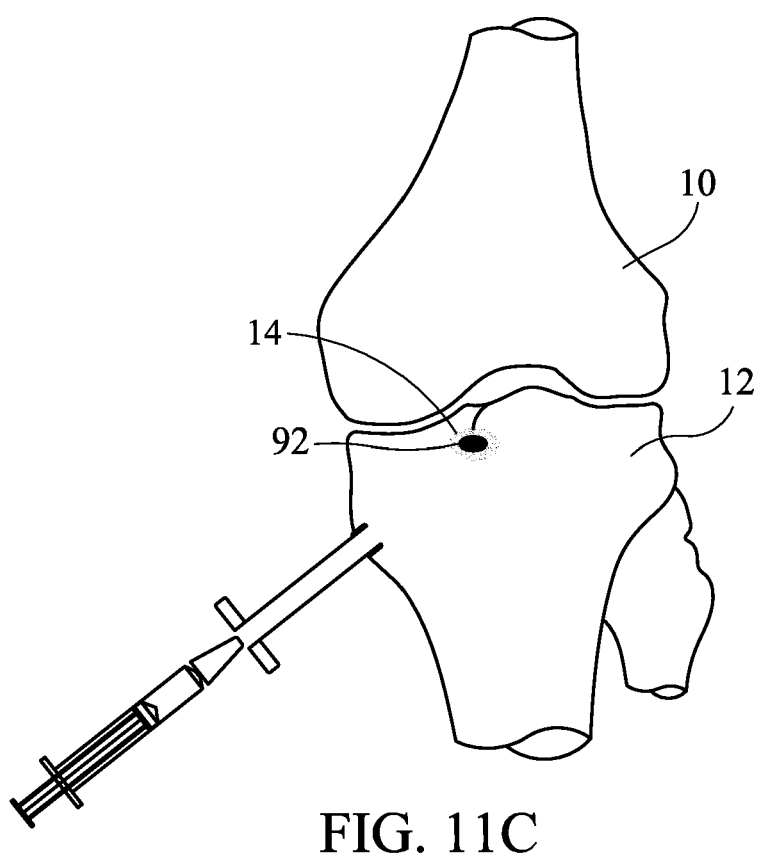

FIGS. 11A-11C illustrate another step that a surgeon may perform to treat a patient's knee. For example, FIG. 11A shows a side view of surgeon injecting CaP cement in or adjacent to a bone marrow lesion using 8-gauge needles 102. As shown, the 8-gauge needles 102 are guided using SCP™ guide/insertion instrument 40 to converge in or adjacent to bone marrow lesion. Alternatively, as shown in FIG. 11B, once the drills have been inserted, the surgeon may remove the SCP™ guide/insertion instrument 40 (not shown) and guide an 8-gauge needle 102 over the drill to inject CaP cement in or adjacent to the bone marrow lesion. For example, a catheter 66 filled with bone cement is then injected into the bone cavity 96 to fill the cavity and then any interstitial space of surrounding uncompressed cancellous bone.

Figure 12:
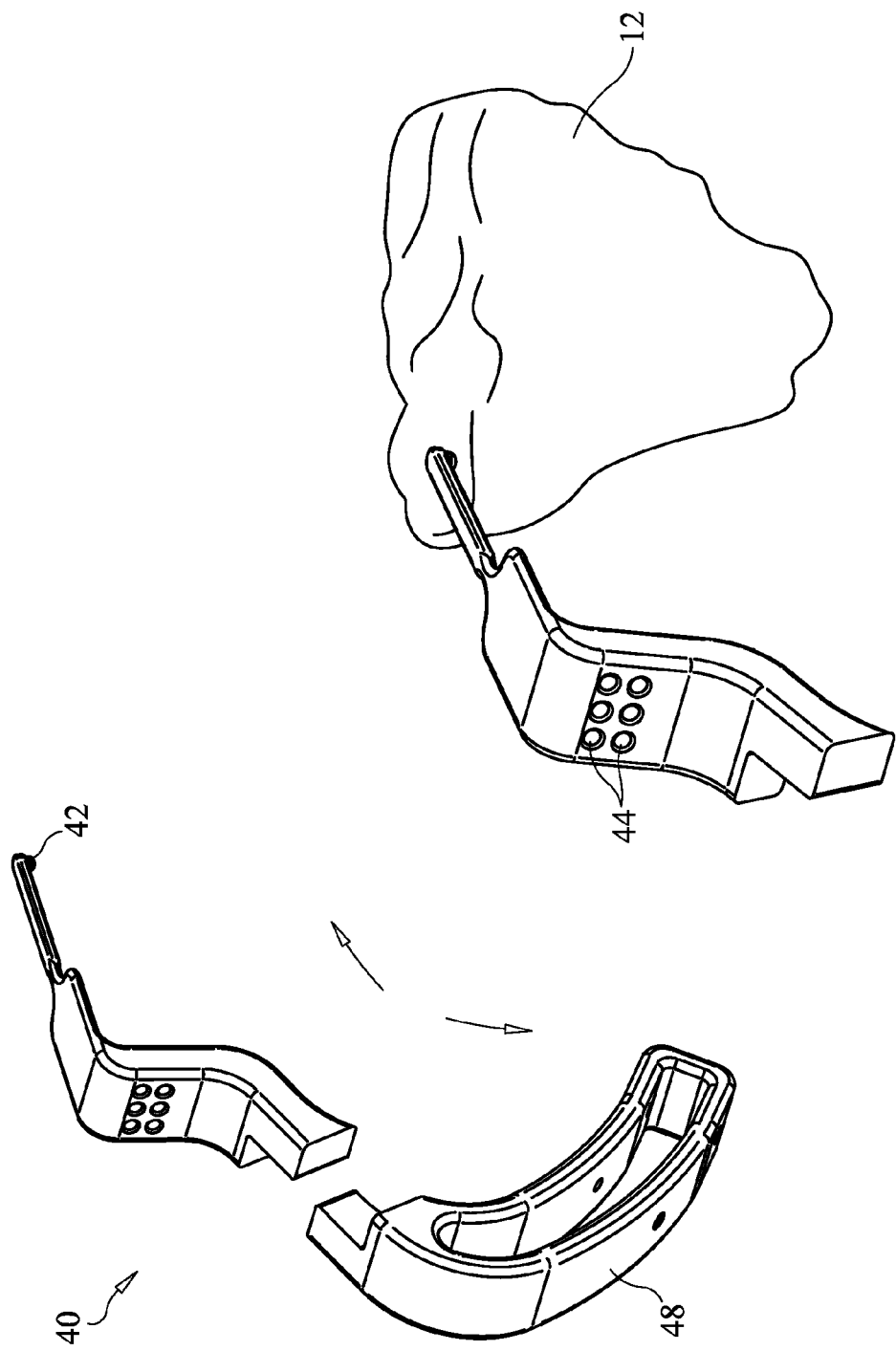
FIGS. 12-16 illustrate a method of treating a subchondral region of a bone based on another embodiment of the present invention.
Figure 13:
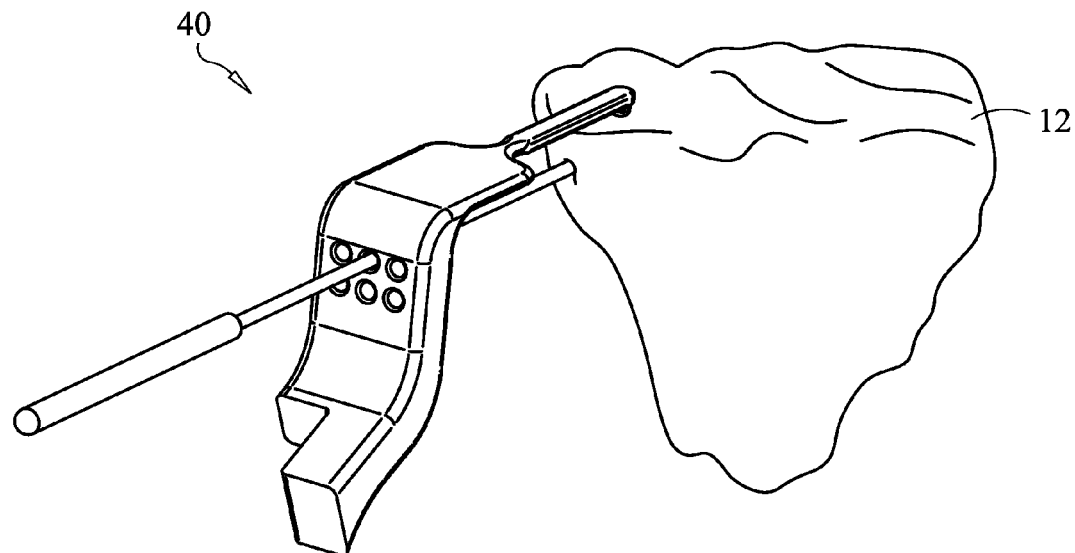

FIGS. 12-16 illustrate a method of treating a bone based on another embodiment of the present invention. In particular, as shown in FIG. 12, the SCP™ guide/insertion instrument 40 may comprise a detachable handle that the surgeon removes initially to position the guide/insertion instrument 40, for example, on the articular surface. Referring now to FIG. 13, the surgeon may then drill via parallel drill/implant guide 44 towards the site of a bone marrow lesion (not shown).

Figure 14:
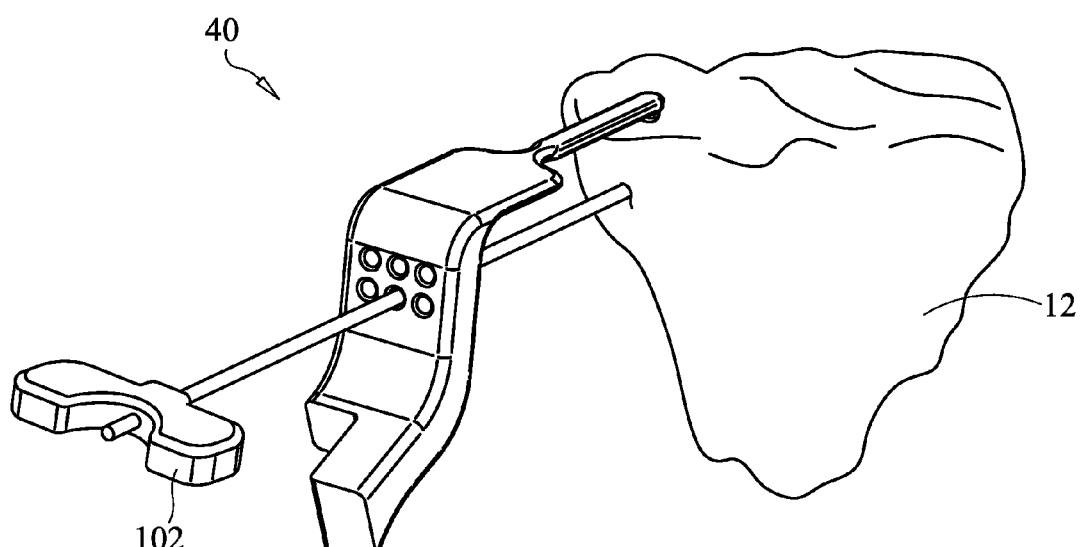
Figure 15:
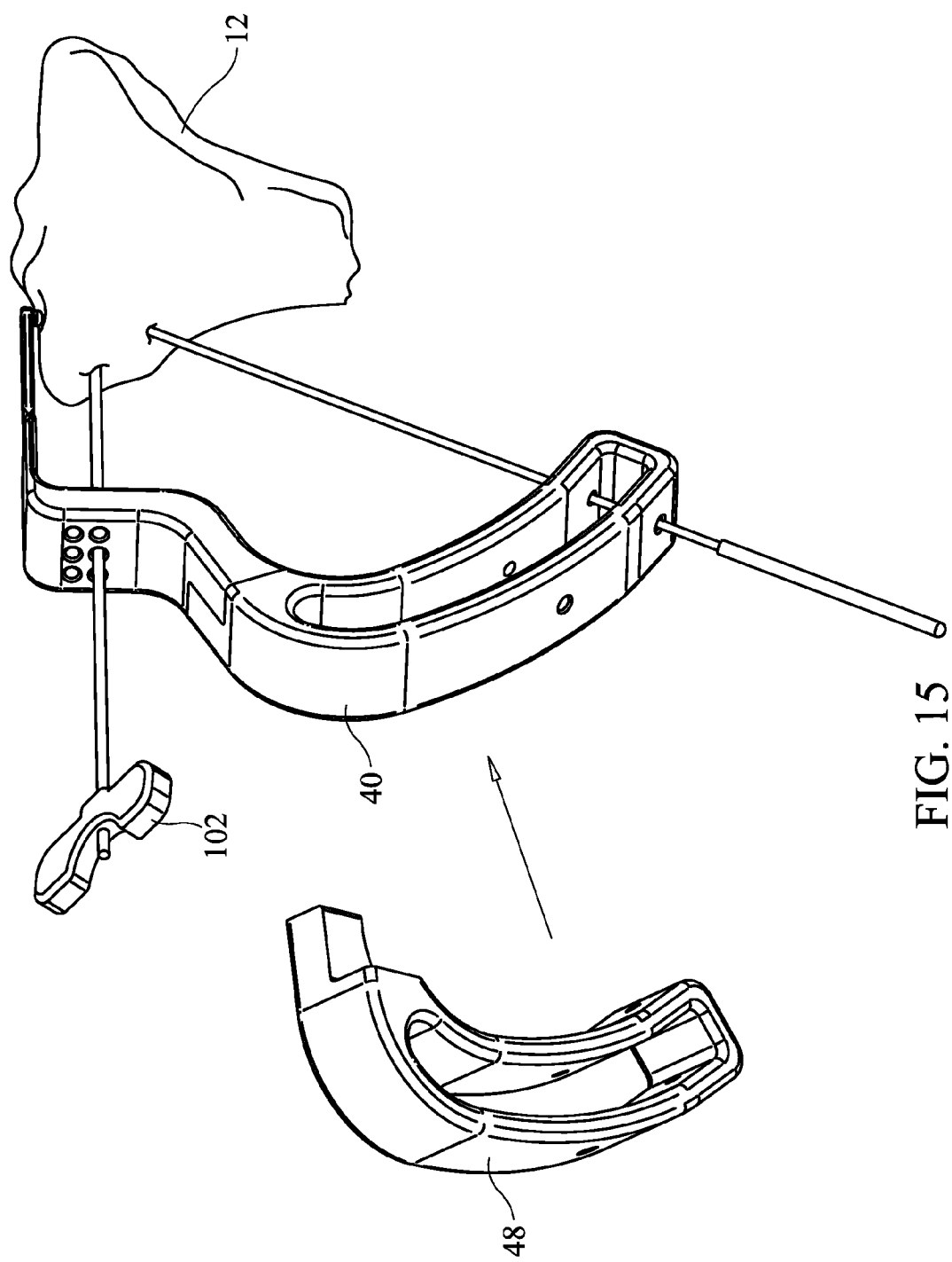
Figure 16:
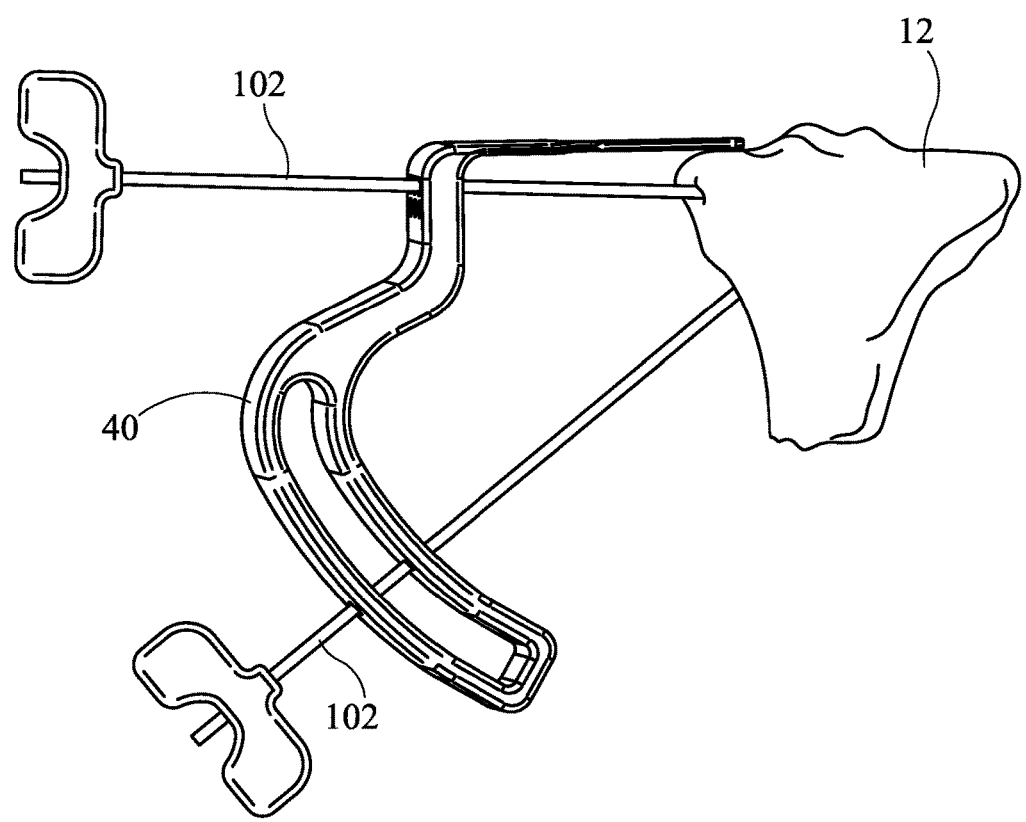

As shown in FIG. 14, the surgeon injects CaP cement using an 8-gauge needle over the drill in or adjacent to the bone marrow lesion. Next, as shown in FIG. 15, the surgeon may reattach the detachable handle 48 to the SCP™ guide/insertion instrument 40 and drill in or through the bone marrow lesion (not shown) via angular drill guide/portal 46. As shown in FIG. 16, if desired, the surgeon may then inject CaP cement using a cannula with injection port or fenestrated distal tip for target placement or dispersion of the bone void filler, or the 8-gauge needle 102, over the drill to inject CaP cement in or adjacent to the bone marrow lesion via angular drill guide/portal 46.

While the invention is described in the context of osteoarthritis of the knee, it is not limited to such condition. Other conditions that can be treated in accordance with the invention include but are not limited to osteoarthritis of joints other than the knee, such as the shoulder, hip and ankle. For example, the SUBCHONDROPLASTY™ treatment may be used to treat other joints, such as the shoulder, hip, and ankle. Moreover, in some embodiments, the SUBCHONDROPLASTY™ treatment may be coupled to other forms of joint pain treatment. For instance, in the knee, the SUBCHONDROPLASTY™ treatment may be employed in conjunction with a microfracture, arthroscopic/arthrosurface, uni-knee replacement, or partial bone resurfacing procedure. In such cases, the SUBCHONDROPLASTY™ procedure itself becomes a component in a multi-step treatment process to address the overall pain management and treatment of the joint.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A system for treating joint pain comprising:
   an injectable material for biological stimulation of a healing response to a subchondral defect in a subchondral region of a bone adjacent to the joint;
   an injector tool for delivery of the material; and
   an instrument for guiding the injector tool, the instrument comprising a guide portion including a plurality of portals configured to guide the injector tool toward the subchondral region for treating the subchondral defect, the guide portion having a reference tip.

2. The system of claim 1, further comprising a cavity creation device for creating an access channel into the subchondral region of the bone.

3. The system of claim 2, wherein the cavity creation device is a drilling tool.

4. The system of claim 1, wherein the injectable material is a bone cement, a bone void filler, or a bone substitute material.

5. The system of claim 4, wherein the injectable material further includes a bone growth stimulating factor.

6. The system of claim 1, wherein the instrument further comprises a handle portion coupled to the guide portion.

7. The system of claim 6, wherein the handle portion includes one or more portals configured to guide the injector tool to the subchondral region of the bone.

8. The system of claim 1, wherein the subchondral defect is a bone marrow lesion or a bone marrow edema.

9. The system of claim 1, wherein the reference tip is configured for placement on the bone without breaching an outer surface of the bone.

10. The system of claim 1, further comprising:
    a K-wire configured for insertion into one of the portals in the guide portion of the instrument, the K-wire configured to form an access path to the subchondral region of the bone containing the subchondral defect; and
    a cannulated boring device configured to form an enlarged access channel to the subchondral region of the bone containing the subchondral defect, the boring device sized to receive the K-wire such that the K-wire can guide the boring device toward the subchondral region of the bone.

11. The system of claim 1, wherein a proximal end of the guide portion, opposite the reference tip, includes a depth stop.

12. The system of claim 11, further comprising a K-wire configured for insertion into one of the portals in the guide portion of the instrument and including a depth stop, wherein contact between the depth stop of the guide portion and the depth stop of the K-wire can position a distal end of the K-wire at a desired depth within the subchondral region of the bone.

13. The system of claim 11, wherein the depth stop on the guide portion is adjustable.

14. The system of claim 1, wherein:
    the portals of the guide portion include a portal axis configured to extend toward the subchondral defect in the subchondral region of the bone, the system further comprising a cavity creation device insertable into one of the portals and configured to create an access channel extending from an outer surface of the bone to the subchondral region of the bone, the injector tool configured for delivery of the material through the access channel for treatment of the subchondral defect.

15. The system of claim 14, wherein the injectable material is a bone cement, a bone void filler, or a bone substitute material.

16. The system of claim 15, wherein the injectable material further includes a bone growth stimulating factor.

17. The system of claim 14, wherein the subchondral defect is a bone marrow lesion or a bone marrow edema.

18. The system of claim 14, wherein the instrument includes at least one marker for identification under imaging.

19. A system for treating joint pain comprising:
    an injectable material for biological stimulation of a healing response to a subchondral defect in a subchondral region of a bone adjacent to the joint, wherein the injectable material is a bone cement, a bone void filler, or a bone substitute material, and wherein the subchondral defect is a bone marrow lesion or a bone marrow edema;
    an injector tool for delivery of the material; and
    an instrument for guiding the injector tool, the instrument comprising a guide portion including a plurality of portals configured to guide the injector tool toward the subchondral region for treating the subchondral defect, the guide portion having a reference tip.

20. The system of claim 19, wherein the reference tip is configured for placement on the bone without breaching an outer surface of the bone.

\* \* \* \* \*

UNITED STATES PATENT AND TRADEMARK OFFICE
CERTIFICATE OF CORRECTION

PATENT NO. : 9,717,544 B2
APPLICATION NO. : 14/617058
DATED : August 1, 2017
INVENTOR(S) : Sharkey et al.

Page 1 of 1

It is certified that error appears in the above-identified patent and that said Letters Patent is hereby corrected as shown below:

On page 4, in Column 2, under "Other Publications", Line 1, delete "May 26," and insert --May 25,-- therefor On page 5, in Column 1, under "Other Publications", Line 58, delete "Apr. 24," and insert --Apr. 25,-- therefor On page 5, in Column 2, under "Other Publications", Line 1, delete "Apr. 3," and insert --Apr. 30,-- therefor Signed and Sealed this
Tenth Day of April, 2018

Andrei Iancu
*Director of the United States Patent and Trademark Office*